US009616051B2

(12) United States Patent
Sullivan et al.

(10) Patent No.: US 9,616,051 B2
(45) **Date of Patent: *Apr. 11, 2017**

(54) DRUG TARGETS TO OVERCOME DE NOVO DRUG-RESISTANCE IN MULTIPLE MYELOMA

(71) Applicants: H. Lee Moffitt Cancer Center and Research Institute, Inc., Tampa, FL (US); University of Florida Research Foundation, Inc., Gainesville, FL (US)

(72) Inventors: Daniel M. Sullivan, Lutz, FL (US); Thomas C. Rowe, Gainesville, FL (US); David A. Ostrov, Gainesville, FL (US); Joel G. Turner, Land O'Lakes, FL (US)

(73) Assignees: H. Lee Moffitt Cancer Center and Research Institute, Inc., Tampa, FL (US); University of Florida Research Foundation, Inc., Gainesville, FL (US)

( * ) Notice: Subject to any disclaimer, the term of this patent is extended or adjusted under 35 U.S.C. 154(b) by 346 days.

This patent is subject to a terminal disclaimer.

(21) Appl. No.: 13/908,339

(22) Filed: Jun. 3, 2013

(65) Prior Publication Data

US 2013/0281389 A1 Oct. 24, 2013

Related U.S. Application Data

(63) Continuation of application No. PCT/US2011/063266, filed on Dec. 5, 2011, and a continuation of application No. 13/159,016, filed on Jun. 13, 2011, which is a continuation of application No. PCT/US2009/067922, filed on Dec. 14, 2009.

(60) Provisional application No. 61/419,536, filed on Dec. 3, 2010, provisional application No. 61/122,098, filed on Dec. 12, 2008.

(51) Int. Cl.

| | |
|---|---|
| ***A61K 31/122*** | (2006.01) |
| ***A61K 31/529*** | (2006.01) |
| ***A61K 31/439*** | (2006.01) |
| ***A61K 31/5395*** | (2006.01) |
| ***A61K 31/4164*** | (2006.01) |
| ***A61K 31/519*** | (2006.01) |
| ***A61K 31/53*** | (2006.01) |
| ***A61K 45/06*** | (2006.01) |
| ***C07C 49/633*** | (2006.01) |
| ***C07D 233/24*** | (2006.01) |
| ***C07D 471/18*** | (2006.01) |
| ***C07D 487/16*** | (2006.01) |
| ***C07D 487/22*** | (2006.01) |

(52) U.S. Cl.

CPC .......... *A61K 31/439* (2013.01); *A61K 31/122* (2013.01); *A61K 31/4164* (2013.01); *A61K 31/519* (2013.01); *A61K 31/529* (2013.01); *A61K 31/53* (2013.01); *A61K 31/5395* (2013.01); *A61K 45/06* (2013.01); *C07C 49/633* (2013.01); *C07D 233/24* (2013.01); *C07D 471/18* (2013.01); *C07D 487/16* (2013.01); *C07D 487/22* (2013.01)

(58) Field of Classification Search

CPC ...... A61K 31/53; A61K 31/529; A61K 31/22; A61K 45/06

See application file for complete search history.

(56) References Cited

U.S. PATENT DOCUMENTS 7,795,457 B2 9/2010 Fu et al.

OTHER PUBLICATIONS

Hazlehurst, et al., Reduction in drug-induced DNA double-strand breaks associated with beta1 integrin-mediated adhesion correlates with drug resistance in U937 cells. Blood 2001; 98:1897-903.

Hazlehurst LA, et al., Cell adhesion to fibronectin (CAM-DR) influences acquired mitoxantrone resistance in U937 cells. Cancer Res 2006; 66:2338-45.

Valkov, et al., Cell density-dependent VP-16 sensitivity of leukaemic cells is accompanied by the translocation of topoisomerase IIalpha from the nucleus to the cytoplasm. Br J Haematol 2000; 108:331-45.

Turner JG, et al., Human topoisomerase IIalpha nuclear export is mediated by two CRM-1-dependent nuclear export signals. J Cell Sci 2004; 117:3061-71.

Turner & Sullivan, CRM1-mediated nuclear export of proteins and drug resistance in cancer. Curr Med Chem 2008; 15: 2648-55.

Cook, et al., Structural biology of nucleocytoplasmic transport. Annu Rev Biochem 2007; 76: 647-71.

Dong, et al., Structural basis for leucine-rich nuclear export signal recognition by CRM1. Nature 2009; 458: 1136-41.

Turner, et al. Human multiple myeloma cells are sensitized to topoisomerase II inhibitors by CRM1 inhibition. Cancer Res 2009; 69: 6899-905.

Engel, et al., The cytoplasmic trafficking of DNA topoisomerase IIalpha correlates with etoposide resistance in human myeloma cells. Exp Cell Res 2004; 295: 421-31.

Newlands, et al., Phase I trial of elactocin. Br J Cancer 1996; 74:648-9.

(Continued)

*Primary Examiner* — Samira Jean-Louis

(74) *Attorney, Agent, or Firm* — Robert J. Varkonyi; Smith & Hopen, P.A.

(57) ABSTRACT

Topoisomerase II alpha (topo IIα) is exported from the cell nucleus in human myeloma cells by a chromosome-maintenance protein-1 (CRM1)-dependent mechanism, resulting in topo II inhibitor resistance. The nuclear export signal (NES) of topo IIα is unique, making it a potential target for small molecule inhibitors. Small molecules NES inhibitors were identified, which inhibited binding of topo IIα to the export receptor CRM1. Inhibition was specific to topo IIα as p53 trafficking was unaffected along with topo IIα protein expression and function (decatenation). These topo IIα-specific nuclear export inhibitors may potentially lead to a new approach in circumventing drug resistance in multiple myeloma. The compounds provide a protocol for treating multiple myeloma or an oncogenic disease. Further, the topoisomerase II nuclear export signal inhibitor may be combined with a topoisomerase II inhibitor.

16 Claims, 15 Drawing Sheets

(56) References Cited

OTHER PUBLICATIONS

Kelley & Sternberg, Protein structure prediction on the Web: a case study using the Phyre server. Nat Protoc 2009; 4: 363-71.
Driscoll, The preclinical new drug research program of the National Cancer Institute. Cancer Treat Rep 1984; 68: 63-76.
Gschwend , et al., Molecular docking towards drug discovery. J Mol Recognit 1996; 9: 175-86.
Ewing, et al. Dock 4.0: search strategies for automated molecular docking of flexible molecule databases. J Comput Aided Mol Des 2001; 15: 411-28.
Pettersen, et al., UCSF Chimera—a visualization system for exploratory research and analysis. J Comput Chem 2004; 25: 1605-12.
Corsino, et al., A novel class of cyclin-dependent kinase inhibitors identified by molecular docking act through a unique mechanism. J Biol Chem 2009; 284: 29945-55.
Homsi, et al., Src activation in melanoma and Src inhibitors as therapeutic agents in melanoma. Melanoma Res 2009; 19: 167-75.
Muller, et al., Single-strand DNA cleavages by eukaryotic topoisomerase II. Biochemistry 1988; 27: 8369-79.
Li Y, Bor YC, Misawa Y, Xue Y, Rekosh D, Hammarskjold ML. An intron with a constitutive transport element is retained in a Tap messenger RNA. Nature 2006; 443: 234-7.
Turner et al. Nuclear export of proteins and drug resistance in cancer. Biochemical Pharmacology 2012; 83: 1021-1032.
National Center for Biotechnology Information. PubChem Compound Database; CID=6719, https://pubchem.ncbi.nlm.nih.gov/compound/6719.
NCI-H929 [H929] (ATCC CRL-9068). *Homo sapiens* bone marrow. http://www.atcc.org/products/all/CRL-9068.aspx. Accessed on Feb. 10, 2016.
MCF7 (ATCC HTB-22). *Homo sapiens* mammary gland, breast; derived from metastatic site: pleural effusion. http://www.atcc.org/products/all/HTB-22.aspx. Accessed on Feb. 10, 2016.
Kutay & Guttinger (2005). Leucine-rich nuclear-export signals: born to be weak. Trends Cell Biol 15(3): 121-124.
Binaschi, et al., Mechanism of action of DNA topoisomerase inhibitors. Stem Cells. Jul. 1995;13(4):369-79.

A

B

C

A

C

D

B

DRUG TARGETS TO OVERCOME DE NOVO DRUG-RESISTANCE IN MULTIPLE MYELOMA

CROSS REFERENCE TO RELATED APPLICATION

This application is a continuation of prior filed International Application, Serial Number PCT/US2011/63266 filed Dec. 5, 2011, which claims priority to U.S. Provisional Patent Application No. 61/419,536, entitled "Novel Drug Targets to Overcome De Novo Drug-Resistance in Multiple Myeloma", filed on Dec. 3, 2010, and U.S. patent application Ser. No. 13/159,016, entitled "Nuclear Export Inhibitors of Topoisomerase II Alpha", filed on Jun. 13, 2011, which claims priority to International Application, Serial Number PCT/US2009/067922, entitled "Nuclear Export Inhibitors of Topoisomerase IIα" filed Dec. 14, 2009, which claims priority to U.S. provisional patent application No. 61/122,098, entitled "Small Molecule Inhibitors of Nuclear Export of Topoisomerase II Alpha for the Treatment of Human Cancer", filed Dec. 12, 2008, the contents of which are herein incorporated by reference.

FIELD OF INVENTION

This invention relates to cancer treatment. Specifically, the invention provides a method of treating multiple myeloma and other oncogenic diseases using novel compounds.

BACKGROUND OF THE INVENTION

Multiple myeloma (MM) is a tumor of terminally-differentiated plasma cells. During development, genetic abnormalities in the forming plasma cells can result in malignant MM cells, which travel through the bloodstream and deposit in bone marrow and other organs, causing the variable symptoms of MM. Initial transformative are thought to occur post-germinal, as suggested by the hypermutation of IGV genes. Collections of abnormal cells accumulate in bones, where they cause bone lesions and elevated calcium levels from myeloma cell release of IL-6, and in the bone marrow where they interfere with the production of normal blood cells, resulting in anemia and impaired immune response. Most cases of myeloma also feature the production of a paraprotein, an abnormal antibody that can cause kidney problems and interferes with the production of normal antibodies leading to immunodeficiency. The disease develops in 1-4 per 100,000 people per year. It is more common in men, and is twice as common in African American populations than it is in Caucasians. With conventional treatment, the prognosis is 3-4 years, which may be extended to 5-7 years with advanced treatments. Multiple myeloma is the second most common hematological malignancy (13%) and constitutes 1% of all cancers.

MM is diagnosed with blood tests, such as electrophoresis, peripheral blood smear, and microscopic examination of the bone marrow. Standard treatments include lenalidomide, bortezomit, thalidomite, doxirubicin, melphalan, cyclosphamide, prednisone, or dexamethasone. The disease is thought to progress due to dysregulation of the apoptotic mechanisms in plasma cells, which also is likely responsible for the resultant chemoresistance.

MM still remains an incurable disease despite improved treatment regimens that include bortezomib, lenalidomide and thalidomide. Other treatments that are thought to cause remission include steroids, chemotherapy, and stem cell transplants. Drug resistance, including resistance to topoisomerase II (topo II) inhibitors, is a major obstacle in the treatment of multiple myeloma. Cell adhesion-mediated drug resistance and stromal cell adherence are important parameters in the local bone marrow environment in patients with multiple myeloma and appear to be major determinants of drug resistance (Hazlehurst, et al., Reduction in drug-induced DNA double-strand breaks associated with beta1 integrin-mediated adhesion correlates with drug resistance in U937 cells. Blood 2001; 98:1897-903; Hazlehurst L A, et al., Cell adhesion to fibronectin (CAM-DR) influences acquired mitoxantrone resistance in U937 cells. Cancer Res 2006; 66:2338-45). Additionally, human multiple myeloma cell density is a determinant of sensitivity to topo II inhibitors (Valkov, et al., Cell density-dependent VP-16 sensitivity of leukaemic cells is accompanied by the translocation of topoisomerase IIalpha from the nucleus to the cytoplasm. Br J Haematol 2000; 108:331-45; Turner J G, et al., Human topoisomerase IIalpha nuclear export is mediated by two CRM-1-dependent nuclear export signals. J Cell Sci 2004; 117:3061-71). At increased cell densities, a considerable fraction of nuclear topo IIα(>90%) is exported to the cytoplasm, resulting in chemoresistance to VP-16 and doxorubicin. This appears to occur both in human myeloma cell lines and in CD138+ cells isolated from patients with multiple myeloma. Intracellular mislocalization of tumor suppressor or nuclear drug target has been shown to decrease the effectiveness of antineoplastic agents, such as with the tumor suppressors and chemotherapeutic targets p53, APC/β-catenin, FOXO, p21CIP1, p27KIP1, and topoisomerases I and II (Turner & Sullivan, CRM1-mediated nuclear export of proteins and drug resistance in cancer. Curr Med Chem 2008; 15: 2648-55).

For proteins greater than 60 kDa to be exported to the cytoplasm, they must be transported through the nuclear-pore complex (Cook, et al., Structural biology of nucleocytoplasmic transport. Annu Rev Biochem 2007; 76: 647-71). This transport mechanism involves the binding of chromosome-maintenance protein-1 (CRM1) to a leucine-rich nuclear export signal (NES) on the target protein. This complex is then transported through the nuclear pore into the cytoplasm (Dong, et al., Structural basis for leucine-rich nuclear export signal recognition by CRM1. Nature 2009; 458: 1136-41).

In multiple myeloma (MM), de novo drug resistance to topoisomerase (topo) II poisons occurs at high cell densities due to trafficking of topo IIα from the nucleus to the cytoplasm where it is no longer in contact with the DNA and thus unable to induce cell death (Turner, et al., Human topoisomerase IIalpha nuclear export is mediated by two CRM-1-dependent nuclear export signals. J Cell Sci 2004; 117: 3061-71; Turner, et al. Human multiple myeloma cells are sensitized to topoisomerase II inhibitors by CRM1 inhibition. Cancer Res 2009; 69: 6899-905; Valkov, et al., Cell density-dependent VP-16 sensitivity of leukaemic cells is accompanied by the translocation of topoisomerase IIalpha from the nucleus to the cytoplasm. Br J Haematol 2000; 108: 331-45; Engel, et al., The cytoplasmic trafficking of DNA topoisomerase IIalpha correlates with etoposide resistance in human myeloma cells. Exp Cell Res 2004; 295: 421-31). Topo IIα was previously demonstrated to be exported from the nucleus of human myeloma cells by a CRM1-dependent mechanism (Engel, et al., The cytoplasmic trafficking of DNA topoisomerase IIalpha correlates with etoposide resistance in human myeloma cells. Exp Cell Res 2004; 295: 421-31), and the NES for topo IIα was located to amino acids 1017-28 (site A) and 1054-66 (site B) (Turner, et al., Human topoisomerase IIalpha nuclear export is mediated by two CRM-1-dependent nuclear export signals. J Cell Sci 2004; 117: 3061-71). Blocking nuclear export with a CRM1 inhibitor or by siRNA has been shown to sensitize drug-resistant MM cells to topo II poisons (Turner, et al., Human multiple myeloma cells are sensitized to topoisomerase II inhibitors by CRM1 inhibition. Cancer Res 2009; 69: 6899-905).

However, use of CRM1 inhibition in cancer therapy has met with limited success. The first CRM1 inhibitor, leptomycin B, was found to efficiently inhibit nuclear export, but showed acute relative toxicities both in a human phase I trial (Newlands, et al., Phase I trial of elactocin. Br J Cancer 1996; 74:648-9) and in vitro. Leptomycin B in vitro studies found acute toxicity at concentrations <5 nmol/L for 1 hour. As such, new therapeutic targets are needed to further improve treatment outcomes of multiple myeolma.

SUMMARY OF THE INVENTION

Mislocalization of topo IIα from the nucleus to the cytosol can render it ineffective as a chemotherapeutic target. High-density myeloma cells were shown to export topo IIα into the cytoplasm, both in vivo and in vitro (Turner, et al., Human topoisomerase IIalpha nuclear export is mediated by two CRM-1-dependent nuclear export signals. J Cell Sci 2004; 117: 3061-71; Valkov, et al., Cell density-dependent VP-16 sensitivity of leukaemic cells is accompanied by the translocation of topoisomerase IIalpha from the nucleus to the cytoplasm. Br J Haematol 2000; 108: 331-45; Engel, et al. The cytoplasmic trafficking of DNA topoisomerase IIalpha correlates with etoposide resistance in human myeloma cells. Exp Cell Res 2004; 295: 421-31). This nuclear export of topo IIα contributes to drug resistance (Engel, et al., The cytoplasmic trafficking of DNA topoisomerase IIalpha correlates with etoposide resistance in human myeloma cells. Exp Cell Res 2004; 295: 421-31), which is not due to differences in drug uptake, cell cycle, or total cellular topo IIα protein levels. In addition, topo IIα nuclear export has been shown to be CRM1 mediated, and topo IIα protein has been found to contain two functional NES located at amino acids 1017-28 (site A) and 1054-66 (site B) (Turner, et al., Human topoisomerase IIalpha nuclear export is mediated by two CRM-1-dependent nuclear export signals. J Cell Sci 2004; 117: 3061-71). Export mediated by both signals was blocked by treatment of the cells with leptomycin B, indicating that a CRM1-dependent pathway mediates export (Turner, et al., Human topoisomerase IIalpha nuclear export is mediated by two CRM-1-dependent nuclear export signals. J Cell Sci 2004; 117: 3061-71).

In MM, CRM1-mediated localization of topo IIα to the cytoplasm prevents formation of lethal drug-induced topo II DNA strand breaks. Evidence suggests that agents blocking nuclear export of topo IIα can reverse drug resistance to topo II poisons. A significant drawback of CRM1 inhibitors to prevent topo IIα export is that they non-specifically block export of any nuclear protein exported by this pathway. To circumvent this shortcoming, computer-generated molecular modeling was used to screen the NCI database for compounds that selectively bind to the NES sites (1017-1028) of topo IIα. Topo IIα's NES site A conforms to the hydrophobic amino acid motif for a NES (Engel, et al., The cytoplasmic trafficking of DNA topoisomerase IIalpha correlates with etoposide resistance in human myeloma cells. Exp Cell Res 2004; 295: 421-31), but does not occur in any other human protein. In addition, this NES is in a pocket formed by the three-dimensional structure of the topo IIα protein. These factors were used to identify drugs that exclusively block the NES of topo IIα and not affect the CRM 1-dependent export of other nuclear proteins.

As such, a method is described herein for treating multiple myeloma or an oncogenic disease through administration of a therapeutically effective amount of a topoisomerase II nuclear export signal inhibitor to a patient. Exemplary topoisomerase II nuclear export signal inhibitors include NCI-36400, NCI-35847, NCI-80640, NCI-9138, NCI-155877, and NCI-35024. In other variations of the invention, the topoisomerase II nuclear export signal inhibitors are

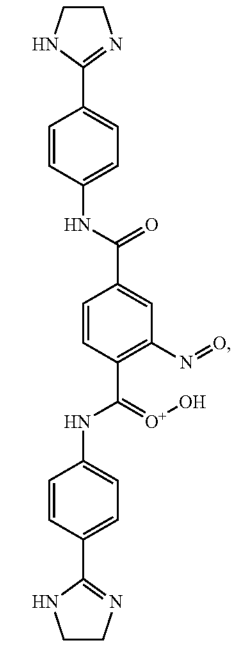

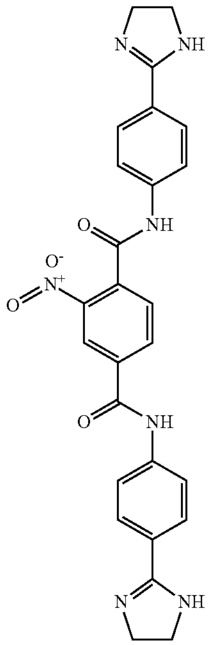

,

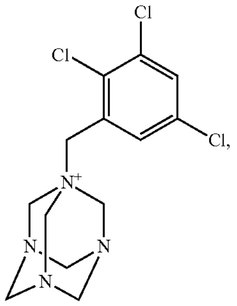

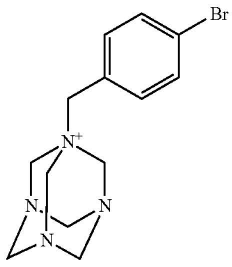

,

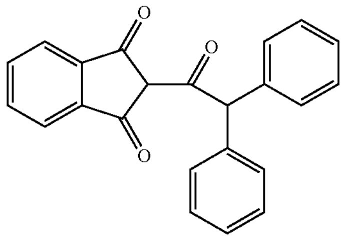

-continued

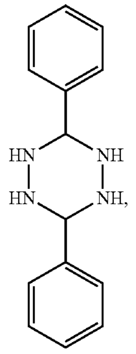

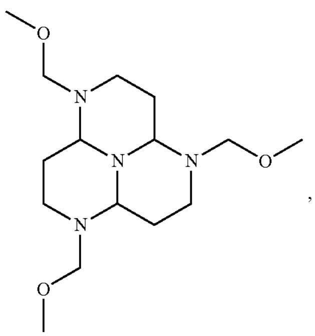

, or

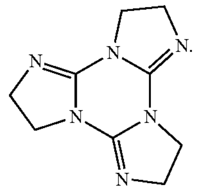

The topoisomerase II nuclear export signal inhibitor is optionally administered at a low micromolar concentration. Exemplary concentrations include 2 μM, 3 μM, 4 μM 5 μM, 10 μM, 15 μM, 20 μM, and 25 μM.

The identified topo isomerase II nuclear export signal inhibitors are expected to only interfere with Crm1-mediated nuclear export of topo IIα. Several of these small molecule inhibitors sensitized cells to the topo II poison doxorubicin, in a synergistic manner. In vitro cytotoxicity and apoptosis assays indicated that these drugs may be effective as single agents or in combination with currently used cancer drugs that target topo II. As such, the topoisomerase II nuclear export signal inhibitors are optionally combined with a topoisomerase II inhibitor, either concurrently or sequentially. Where the topoisomerase II nuclear export signal inhibitor and topoisomerase II inhibitor are administered sequentially, the topoisomerase II inhibitor is optionally administered about 4 hours after the topoisomerase II nuclear export signal inhibitor. For example, the topoisomerase II inhibitor may be administered 1 hour, 1.5 hours, 2 hours, 2.5 hours, 3 hours, 3.5 hours, or 4 hours after the topoisomerase II nuclear export signal inhibitor. Non-limiting examples of the topoisomerase II inhibitor include amsacrine, etoposide, etoposide phosphate, teniposide, doxorubicin, VP-16, VM-26, mitoxantrone, epirubicin, daunomycin, mitoxantrone, and idarubicin. In specific variations, the topoisomerase II inhibitor is administered in the range of about 0.01 to about 200 mg/m2/day for a human. For example, doxorubicin may be administered at 30-60 mg/m2/day, while daunomycin is administered at 45-90 mg/m2/day. The drug may also be administered at up to 500 mg/m2/day. Examples include 50 mg/m2/day, 75 mg/m2/day, 90 mg/m2/day, 93 mg/m2/day, 100 mg/m2/day, 125 mg/m2/day, 150 mg/m2/day, 200 mg/m2/day, 250 mg/m2/day, 300 mg/m2/day, 350 mg/m2/day, 400 mg/m2/day, or 450 mg/m2/day. Of particular note, the NES inhibitors may be used with doxol, doxorubicin, or eptosidoside, and synergistically act with some or all of these compounds.

Immunofluorescence microscopy and cell fractionation studies demonstrated that the NES inhibitors that target site A prevented nuclear export of topo IIα. As such, therapeutically effective amount of a topoisomerase II nuclear export signal inhibitor is contacted on a cell to inhibit topoisomerase II export from a cell nucleus. The topoisomerase II nuclear export signal inhibitor is the NCI-36400, NCI-35847, NCI-80640, NCI-9138, NCI-155877, or NCI-35024. The topoisomerase II nuclear export signal inhibitor is optionally administered at 25 μM. Contacting cell with the topoisomerase II nuclear export signal inhibitor inhibited nuclear export in a topo IIα-specific manner. Testing showed that the topoisomerase II nuclear export signal inhibitors did not prevent export of p53, a protein that is also exported by CRM1. Immunopreciptation data also indicated that the NES inhibitors prevented binding of topo IIα to the nuclear export molecule CRM1. None of the compounds affected topo II decatenation activity or topo IIα protein expression.

BRIEF DESCRIPTION OF THE DRAWINGS

For a fuller understanding of the invention, reference should be made to the following detailed description, taken in connection with the accompanying drawings, in which.

Figure 1:
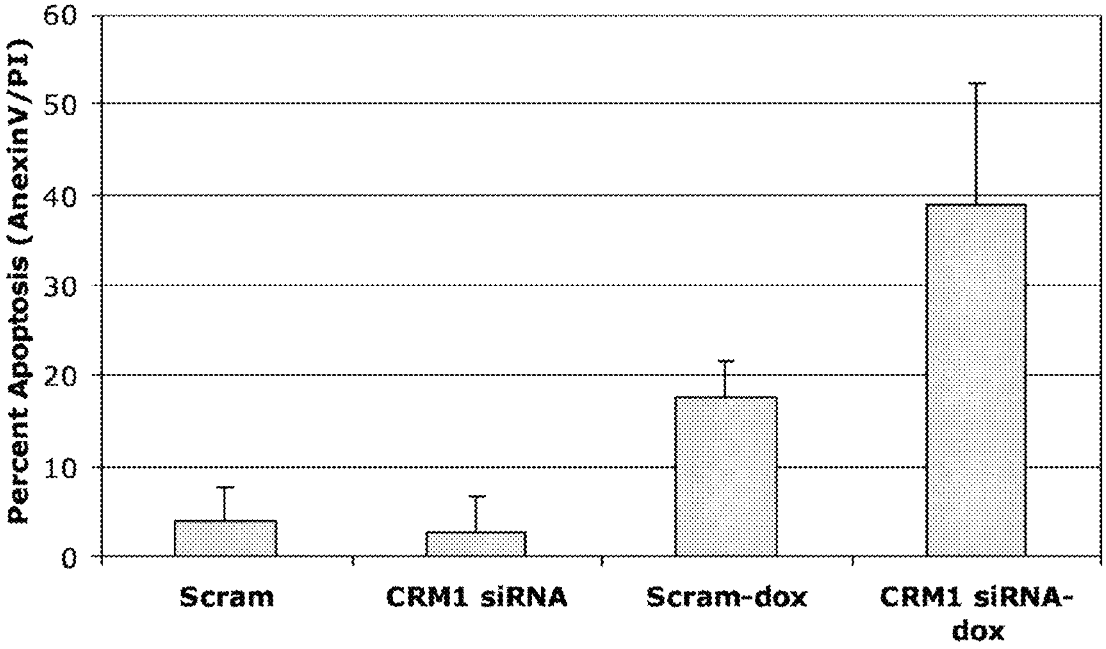
FIG. 1 is a graph showing CRM1 siRNA knockdown makes myeloma cells more sensitive to chemotherapy. Cell transfected with CRM1 siRNA, and treated with the topo II inhibitor doxorubicin (1 μM) more sensitive to topoisomerase inhibitors.

was combined with doxorubicin (2 μM), bortezomib (10 nM), dexamethasone (10 μM), lenalidomide (10 μM), melphalan (10 μM), and topotecan (10 μM). Synergism was seen with doxorubicin.

FIGS. 9(A)-(E) are immunohistochemistry images of H929 cells treated with a topo II NES site A inhibitor. H929 cells were treated for 20 hours with (A) a 0.1% DMSO vehicle, (B) NCI-35847, (C) NCI-80640, (D) NCI-9138, or (E) NCI-155877 and stained with DAPI (light gray) and Alexa 594 (dark gray).

FIG. 10(A)-(F) are images showing the present compounds prevent nuclear export of Topo IIα. Human MM cells were treated with 25 μM of NES inhibitor (A), (B) NCI-36400; (C), (D) NCI-35024; and (E), (F) NCI-35847 and placed at plateau densities (2×106) for 20 hours. Cells were fixed and stained with DAPI (dark gray) and topo IIα antibody Kis1 (light gray). Cell fields are combined DAPI and Kis1 (A), (C), (E) versus Kis1 only signal (B), (D), (F).

Figure 11:
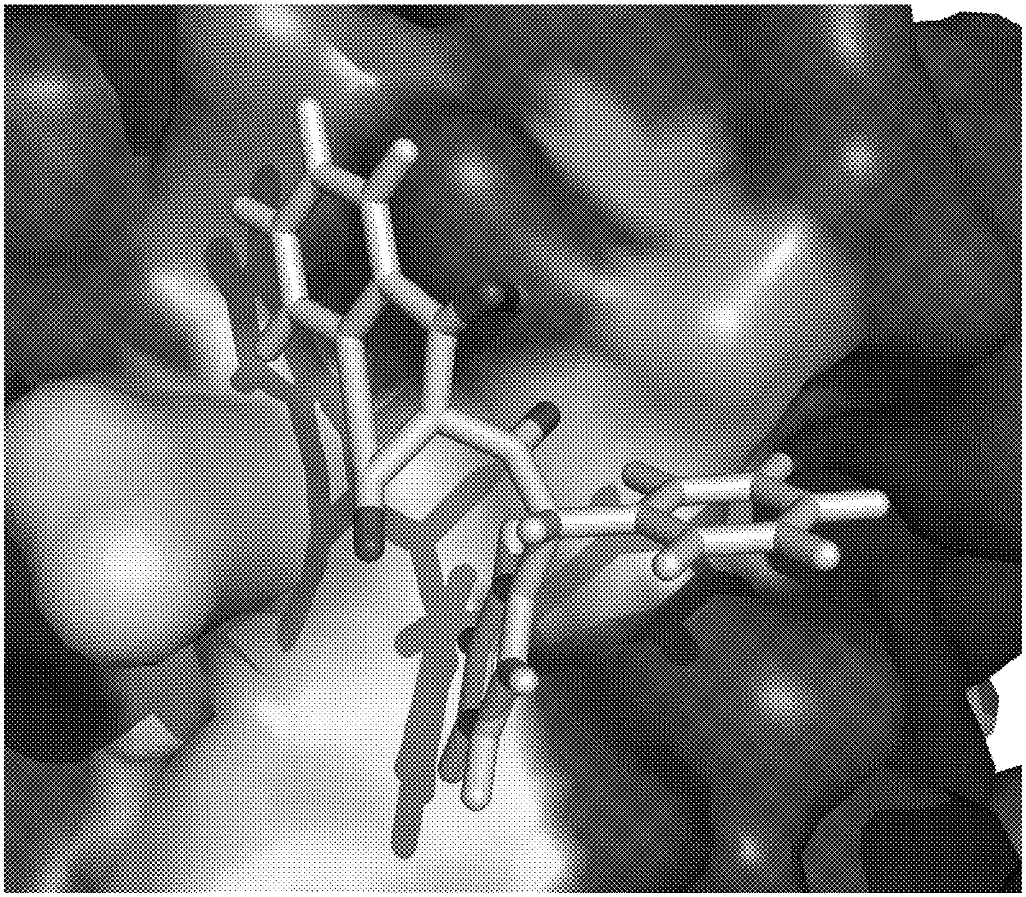

FIG. 11 is a molecular docking model of compound NCI-9138 to the NES of topo IIα.

Figure 12:
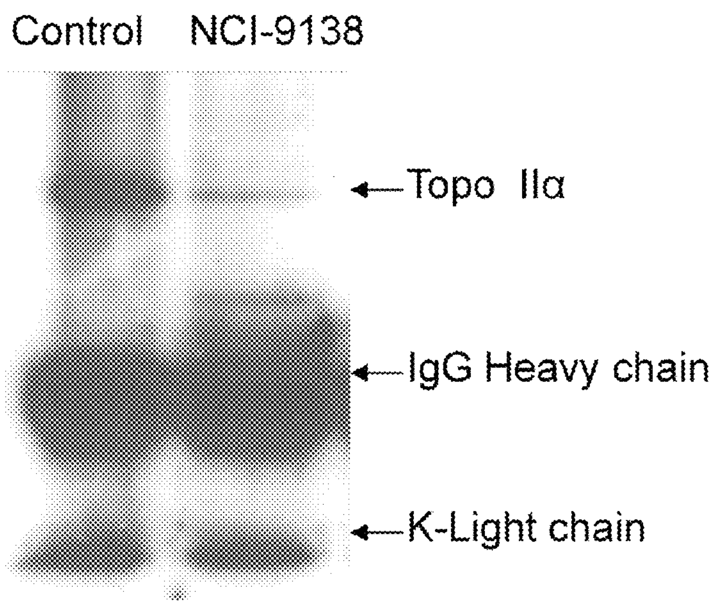

FIG. 12 is a blot from co-immunoprecipitation of chromosome-maintenance protein-1 (CRM1) with topo IIα. CRM-1 is blocked by the NES inhibitor NCI-9138 (50 μM for 20 hours).

Figure 13:
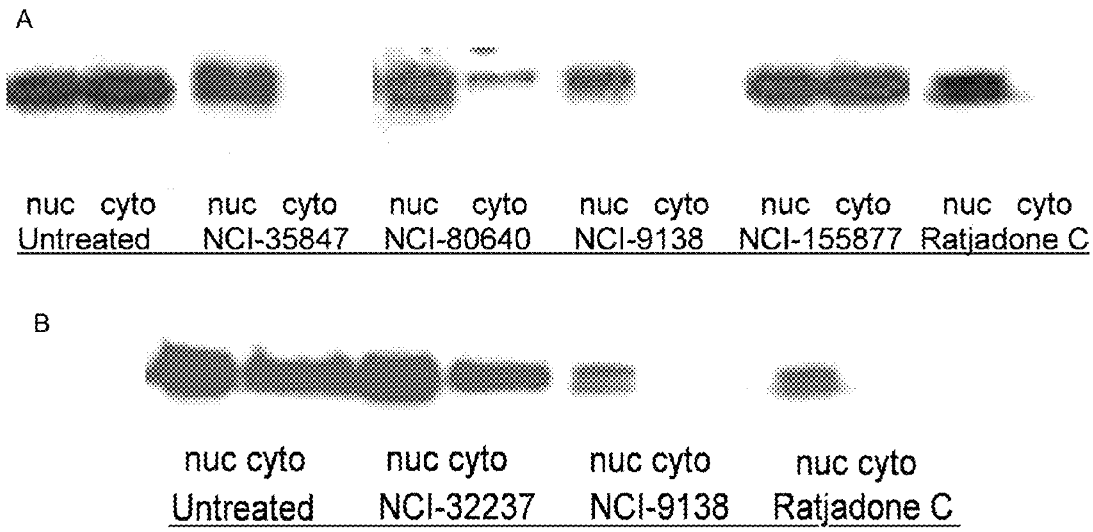

FIGS. 13(A) and (B) are blots from nuclear (nuc)-cytoplasmic (cyto) fractionation of high-density MM cells (n=2). Based on IC50 and apoptosis data, 4 lead compounds were tested for anti-export activity of topo IIα and compared to the anti-export activity of ratjadone C, a CRM1-specific export inhibitor. Human myeloma RPMI-H929 cells were treated for 24 hours. Cells were then chemically separated into nuclear and cytoplasmic fractions. (A) Compounds NCI-35847 and NCI-9138 (25 μM) strongly blocked export of topo IIα, while NCI-80640 and NCI-155877 had a smaller or little effect on topo II nucleus export inhibition. (B) Similar testing confirmed the inhibitory effect of NCI-9138 while NCI-32237, a control compound did not affect nuclear export of topo II. Ratjadone C, a CRM1-specific export inhibitor also prevented nuclear export.

Figure 14:
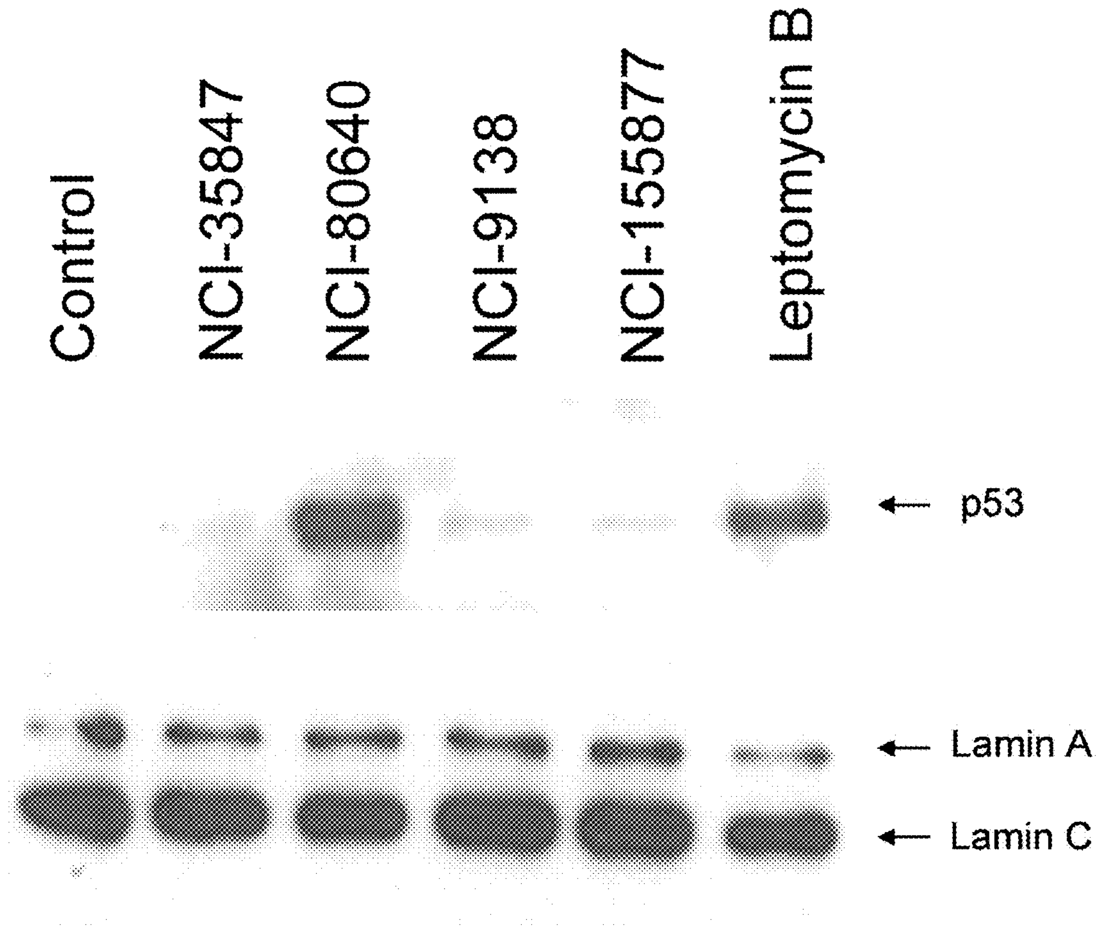

FIG. 14 is a blot of lead compounds tested to determine if nuclear export inhibition was specific to topo IIα protein. p53 was cycled from the nucleus into the cytoplasm in MM cells cultured at log growth conditions. Cells grown at log-phase concentrations were treated with the lead NES inhibitors (25 μM) or a leptomycin control for 20 hours and chemically fractionated. Nuclei were assayed by SDS-PAGE Western blot analysis for p53 protein (anti-p53 (DO-1), Santa Cruz Biotech, Inc). NCI compounds 35847, 9138, and 155877 did not prevent export of p53. Lamin A/C (anti-lamin A/C, BD Pharmingen) is shown as a loading control.

Figure 15:
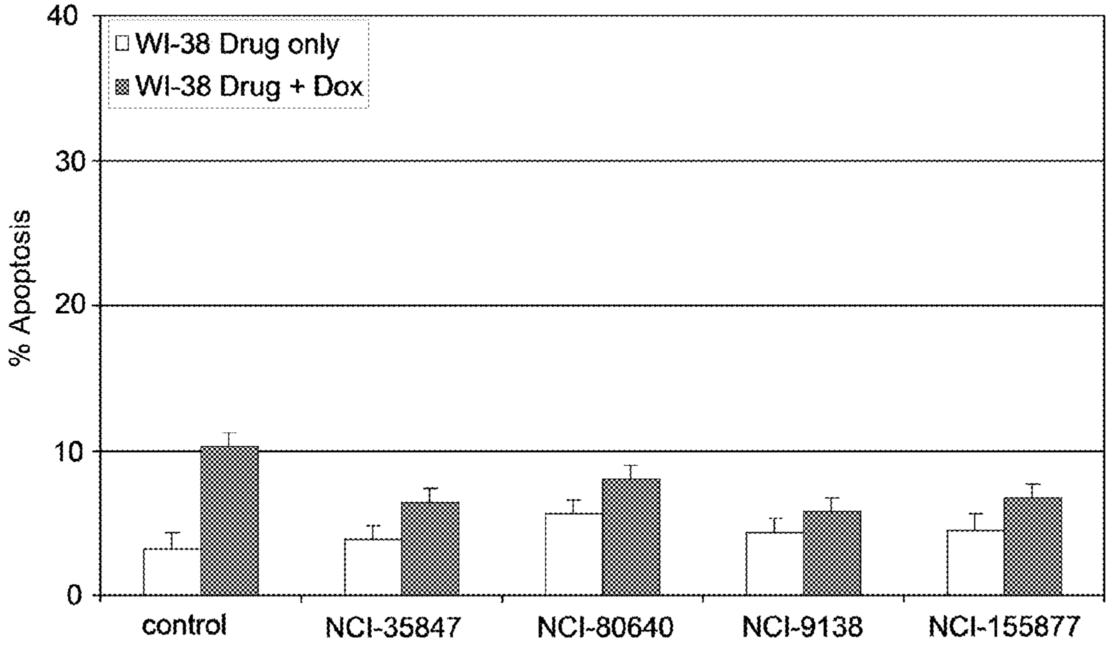

FIG. 15 is a graph showing synergy between the NES inhibitors (25 μM) with the topo II drug doxorubicin (2 μM) was measured by cleaved caspase 3 antibody staining and flow cytometry for high-density normal cells WI-38. Normal fibroblasts WI-38 cells were not sensitive to NES inhibitors and doxorubicin.

Figure 16:
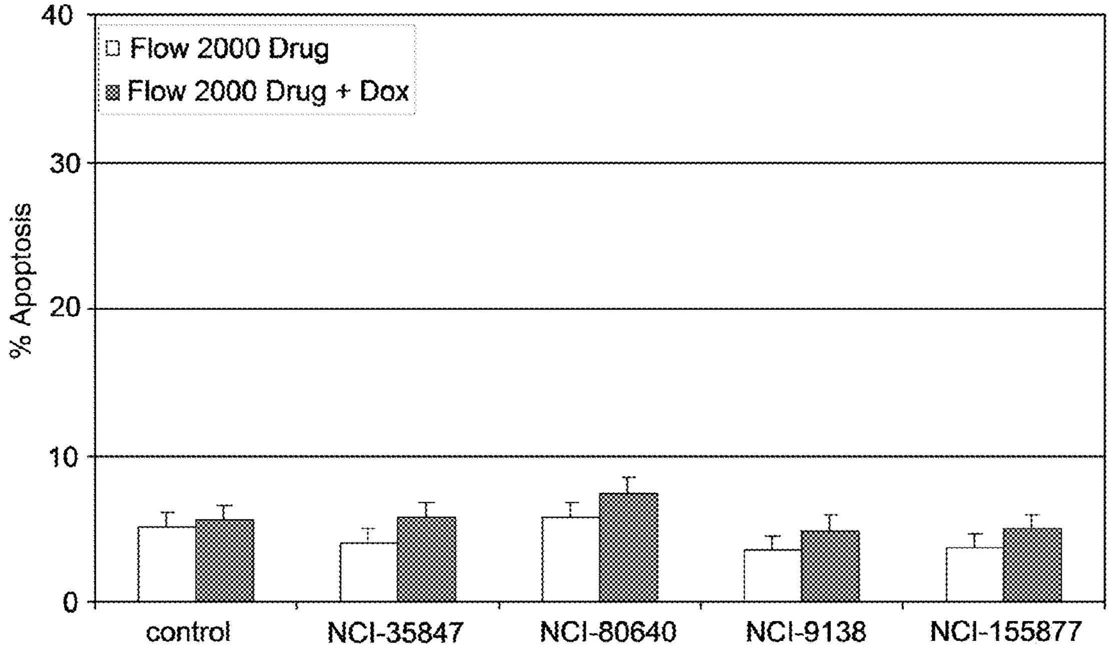

FIG. 16 is a graph showing synergy between the NES inhibitors (25 μM) with the topo II drug doxorubicin (2 μM) was measured by cleaved caspase 3 antibody staining and flow cytometry for high-density normal cells Flow 2000. Normal fibroblast Flow 2000 cells were not sensitive to NES inhibitors and doxorubicin.

Figure 17:
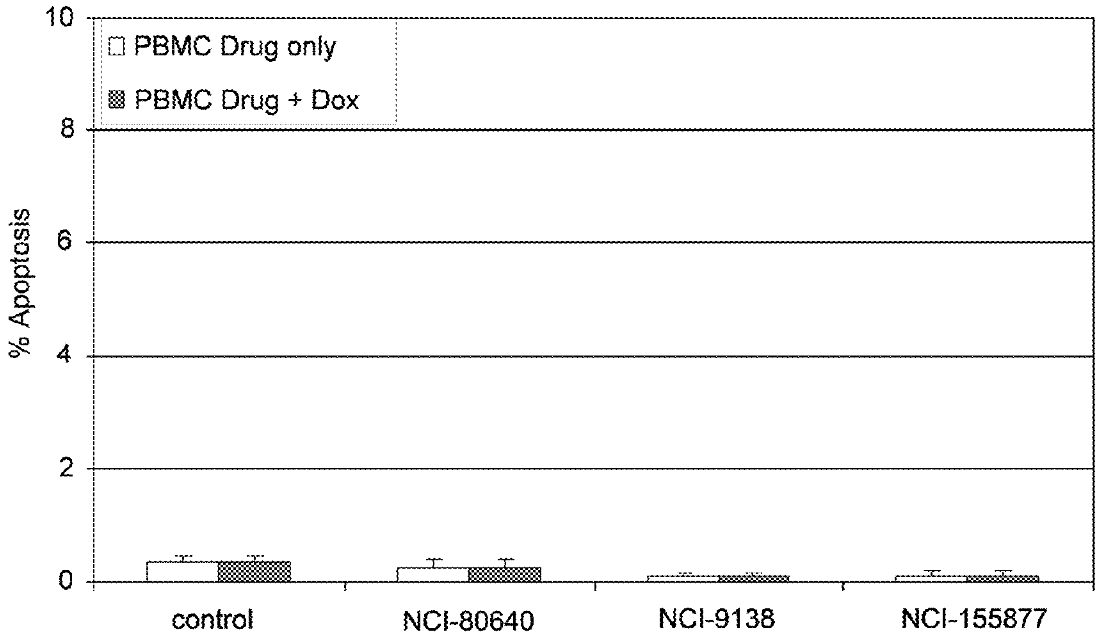

FIG. 17 is a graph showing synergy between the NES inhibitors (25 μM) with the topo II drug doxorubicin (2 μM) was measured by cleaved caspase 3 antibody staining and flow cytometry for high-density normal cells PBMCs. Normal PBMCs were not sensitive to NES inhibitors and doxorubicin.

Figure 18:
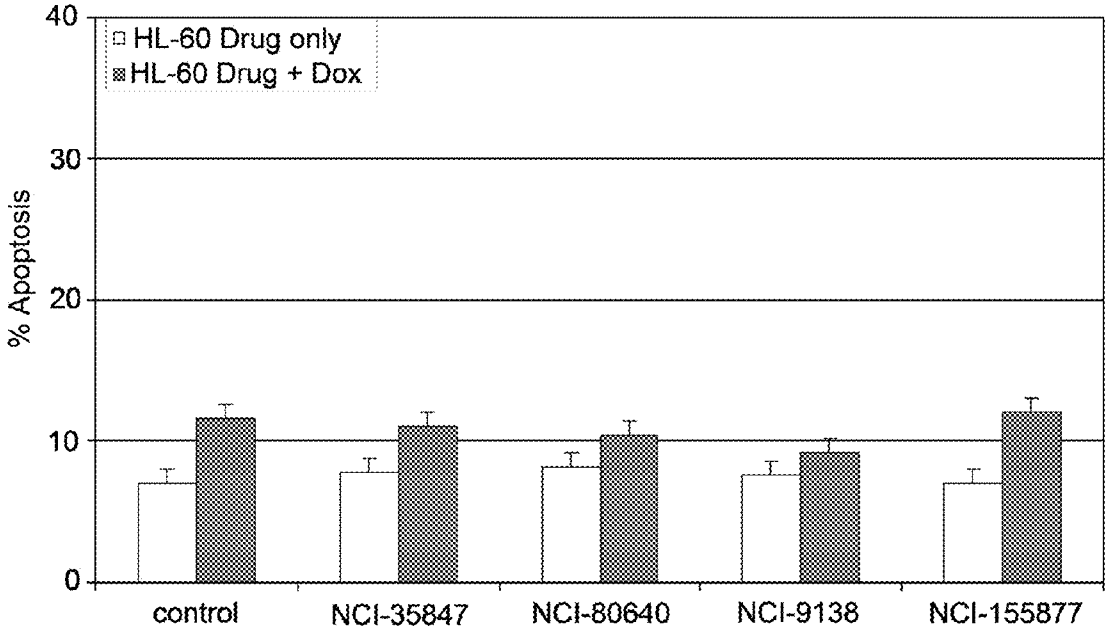

FIG. 18 is a graph showing synergy between the NES inhibitors (25 μM) with the topo II drug doxorubicin (2 μM) was measured by cleaved caspase 3 antibody staining and flow cytometry for cancer cell line HL-60. HL-60 were not sensitive to NES inhibitors and doxorubicin.

Figure 19:
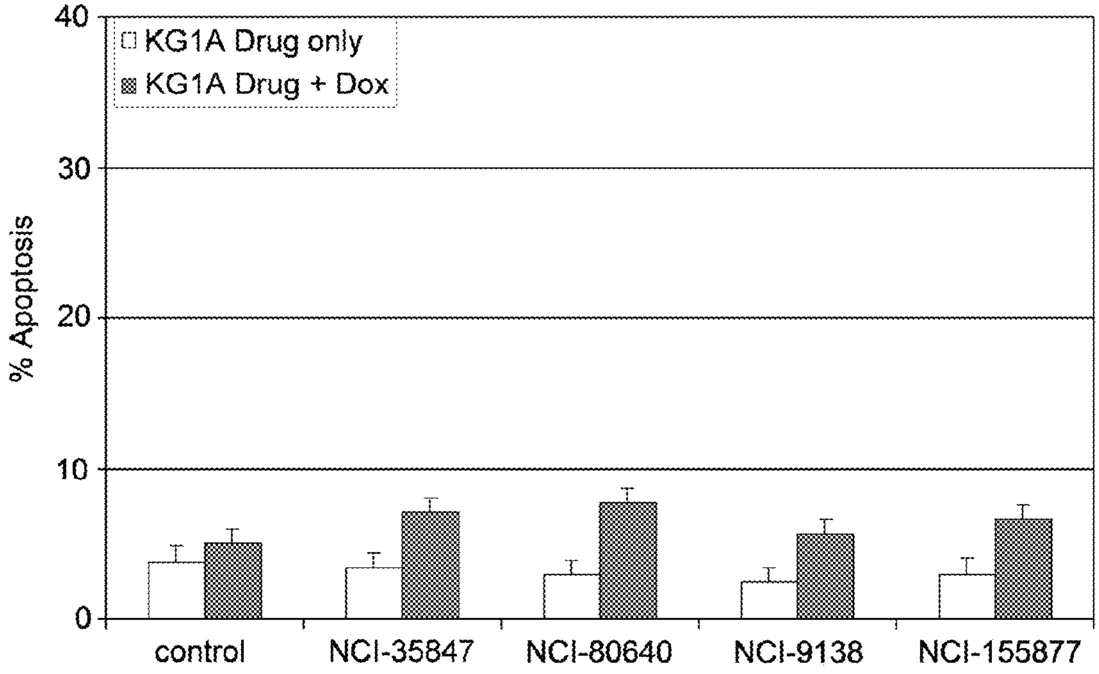

FIG. 19 is a graph showing synergy between the NES inhibitors (25 μM) with the topo H drug doxorubicin (2 μM) was measured by cleaved caspase 3 antibody staining and flow cytometry for cancer cell line KG1a. KG1a were not sensitive to NES inhibitors and doxorubicin.

Figure 20:
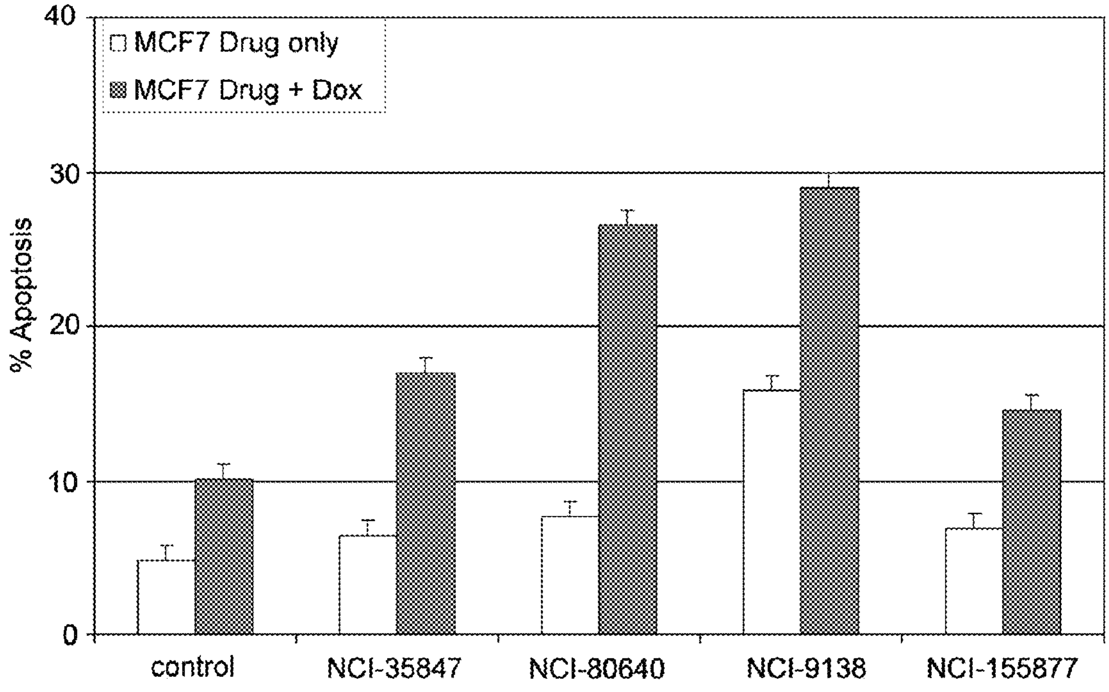

FIG. 20 is a graph showing synergy between the NES inhibitors (25 μM) with the topo II drug doxorubicin (2 μM) was measured by cleaved caspase 3 antibody staining and flow cytometry for cancer cell line MCF7. The breast cancer cell line MCF7 was sensitive to NES inhibitors and doxorubicin.

DETAILED DESCRIPTION OF THE PREFERRED EMBODIMENT

High-density myeloma cells export topo IIα into the cytoplasm via a CRM1-mediated pathway, both in vivo and in vitro, contributing to drug resistance. Topo IIα protein contains two functional NES located at amino acids 1017-28 (site A) and 1054-66 (site B). Targeting intracellular trafficking of proteins may sensitize cells to antitumor agents, and blocking topoisomerase II alpha (topo IIα) trafficking from the nucleus to the cytoplasm in myeloma cells prevents drug resistance and enhances formation of lethal drug-induced topo II DNA strand breaks. Topoisomerase IIα nuclear export inhibitors are described herein for treating multiple myeloma or an oncogenic disease, such as those listed below, through administration of the compounds to a patient, either alone or in combination with a topoisomerase inhibitor.

As used herein, "oncogenic disease" means a condition brought about by aberration of the cellular growth cycle and/or cellular differentiation. Oncogenic diseases include benign cancers, malignant cancers, and pre-cancerous lesions. The term cancer includes both solid tumors and non-solid cancers such as leukemias. Exemplary oncogenic diseases include multiple myeloma, breast cancer, ovarian cancer, testicular cancer, lung cancer, bronchogenic lung cancer, gastric cancer, soft tissue and osteogenic sarcomas, Ewing's sarcoma, malignant lymphoma (Hodgkin's and non-Hodgkin's), acute myeloblastic leukemia, acute lymphoblastic leukemia, and Kaposi's sarcoma.

Additionally, as used herein "patient", means members of the animal kingdom, including mammals, such as but not limited to, primates including humans, gorillas and monkeys; rodents, such as mice, fish, reptiles and birds. The patient may be any animal requiring therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term “administration” and variants thereof (e.g., “administering” a compound) in reference to a compound of the invention means introducing the compound or a prodrug of the compound into the system of a patient in need of treatment. When a compound of the invention or prodrug thereof is provided in combination with one or more other active agents (e.g., a cytotoxic agent, etc.), “administration” and its variants are each understood to include concurrent and sequential introduction of the compound or prodrug thereof and other agents. A person of ordinary skill in the art may determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case, though there will be instances where higher or lower dosage ranges are merited, and such are within the scope of this invention.

In conducting the treatment method of the present invention, the anti-cancer agent or treatment can be administered in any effective manner known in the art, such as by oral, intravenous, intra-peritoneal, or subcutaneous, depending upon the type of cancer being treated, the type of anti-cancer agent or treatment being used, and the medical judgment of the prescribing physician as based, e.g., on the results of published clinical studies. When the anti-cancer agent or treatment is radiation or a radiochemical, the agent or treatment can be administered in any effective manner known in the art, as described briefly herein, above.

The anti-cancer agent or treatment can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The anti-cancer agent or treatment can be combined together with various pharmaceutically acceptable inert carriers in the form of sprays, creams, salves, suppositories, jellies, gels, pastes, lotions, ointments, and the like. Administration of such dosage forms can be carried out in single or multiple doses. A “pharmaceutically acceptable carrier” is a carrier, such as a solvent, suspending agent or vehicle that is suitable for use with humans and/or animals without undue adverse side effects (such as toxicity, irritation, and allergic response) commensurate with a reasonable benefit/risk ratio. The carrier is provided for delivering the compound or compounds of the present invention to the animal or human, and may be liquid or solid based on the planned manner of administration, and may include liposomes or niosomes. As used herein, “carrier” includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Methods of preparing pharmaceutical compositions are also known in the art. In view of the teaching of the present invention, methods of preparing pharmaceutical compositions comprising both a anti-cancer agent or treatment and an NES inhibitor that sensitizes tumor cells to the pro-apoptotic effects of the anti-cancer agent or treatment will be apparent from the art, from other known standard references, such as Remington’s Pharmaceutical Sciences, Mack Publishing Company, Easton, Pa., 18th edition (1990).

For oral administration of the anti-cancer agent or treatment or the NES inhibitor that sensitizes cells to the pro-apoptotic effects of the anti-cancer agent or treatment, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, active agents may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

The term "treating", "treating cancer", "treatment", or "treatment of cancer" refers to obtaining beneficial or desired clinical results via administration of the present compounds to a mammal afflicted with a cancerous condition. Beneficial or desired clinical results refer to an effect that alleviates the cancerous condition by inhibiting of growth and/or metastasis of the cancer or killing the cancerous cells. This includes, but is not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delay or slowing of cancer progression, amelioration of the cancer state, and remission (whether partial or total). The methods of the invention contemplate any one or more of these aspects of treatment.

The term "about" or "approximately" as used herein means within ±5% of a given value or range. Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("Mn") or weight average molecular weight ("Mw"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Kits for practicing the methods of the invention are further provided. By "kit" is intended any manufacture (e.g., a package or a container) comprising at least one reagent, e.g., an NES inhibitor of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

Topoisomerase inhibitors are agents designed to interfere with the action of topoisomerase (topoisomerase I and II), which control changes in DNA structure by catalyzing the breaking and rejoining of the phosphodiester backbone of DNA strands during the normal cell cycle. Inhibitors are often divided according to which type of enzyme it inhibits. Topoisomerase inhibitors may be administered at any dose known effective in the art, such as in the range of about 0.01 to about 200 mg/m2/day for a human. The range used for topoisomerase II inhibitors may be altered based on the drug, patient, and disease, such as using 0.01 to about 10 mg/m2/day for a human. For example, doxorubicin may be administered at 30-60 mg/m2/day, while daunomycin is administered at 45-90 mg/m2/day. The treatment may be repeated on a daily, bi-weekly, semi-weekly, weekly, or monthly basis. In some embodiments, a treatment period may be followed by a rest period of from one day to several days, or from one to several weeks. In combination with an NES inhibitor, the NES inhibitor and the topoisomerase inhibitor may be dosed on the same day or may be dosed on separate days.

Other cytotoxic, chemotherapeutic or anti-cancer agents, or compounds that enhance the effects of the topo inhibitors may be used without departing from this invention. Such compounds include, for example: alkylating agents or agents with an alkylating action, such as cyclophosphamide (CTX; e.g. CYTOXANϕ), chlorambucil (CHL; e.g. LEUKERAN®), cisplatin (Cis P; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6MP), 6-thiocguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: amifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

Example 1

To date, there are no known agents that target the NES of a specific protein that are being developed to treat cancer. Because drug resistance to topo II inhibitors occurs when topo IIα is trafficked from the nucleus to the cytoplasm where it is no longer in contact with the DNA and unable to induce cell death (Valkov, et al., Cell density-dependent VP-16 sensitivity of leukaemic cells is accompanied by the translocation of topoisomerase IIalpha from the nucleus to the cytoplasm. Br J Haematol 2000; 108: 331-45, Engel, et al., The cytoplasmic trafficking of DNA topoisomerase IIalpha correlates with etoposide resistance in human myeloma cells. Exp Cell Res 2004; 295: 421-31), a specific NES in topo IIα was targeted as an innovative treatment approach in MM. This provides a very focused and potent combination with topo II inhibitors, which may also overcome de novo drug resistance in MM. The nuclear export signals (NES) for topo IIα have also identified at amino acids 1017-28 (site A) and 1054-66 (site B) (Turner et al., Human topoisomerase IIalpha nuclear export is mediated by two CRM-1-dependent nuclear export signals. J Cell Sci 2004; 117: 3061-71). Blocking nuclear export of topo IIα with a CRM1 inhibitor or by siRNA has been shown to sensitize MM cells to topo II poisons, as seen in FIG. 1. Analysis of potential drugs against topoisomerase II was performed based on the unique topo II NES site at 1017-1028. Though this site conforms to the hydrophobic amino acid motif for an NES, the amino acid sequence does not occur in any other human protein. In addition, this NES is in a pocket formed by the three-dimensional structure of the topo IIα protein. These factors were used to development drugs that exclusively block the NES of topo IIα without affecting the export of other nuclear proteins, as occurs with other known CRM1 inhibitors.

Figure 2:
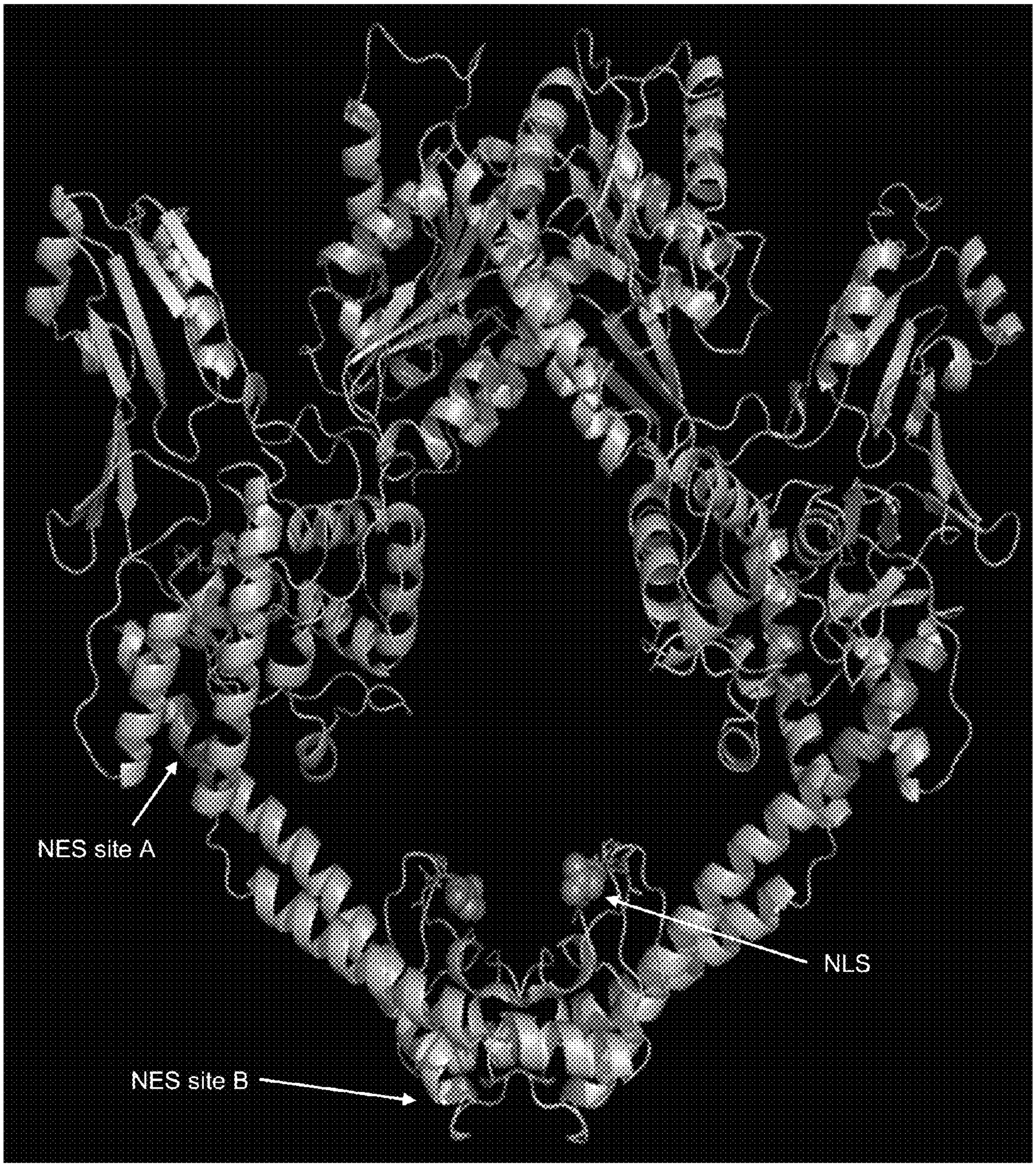
FIG. 2 is a computer image showing how the small molecule inhibitors interact with topo II via nuclear export signal (NES) sites. The structure of *Saccharomyces cerevisiae* topo II was used to create a homology model of human topo IIα using the program PhyreA. Topo IIα is displayed as a gray ribbon diagram, with the NES site A, NES site B, and the nuclear localization signal (NLS) indicated.
Figure 3:
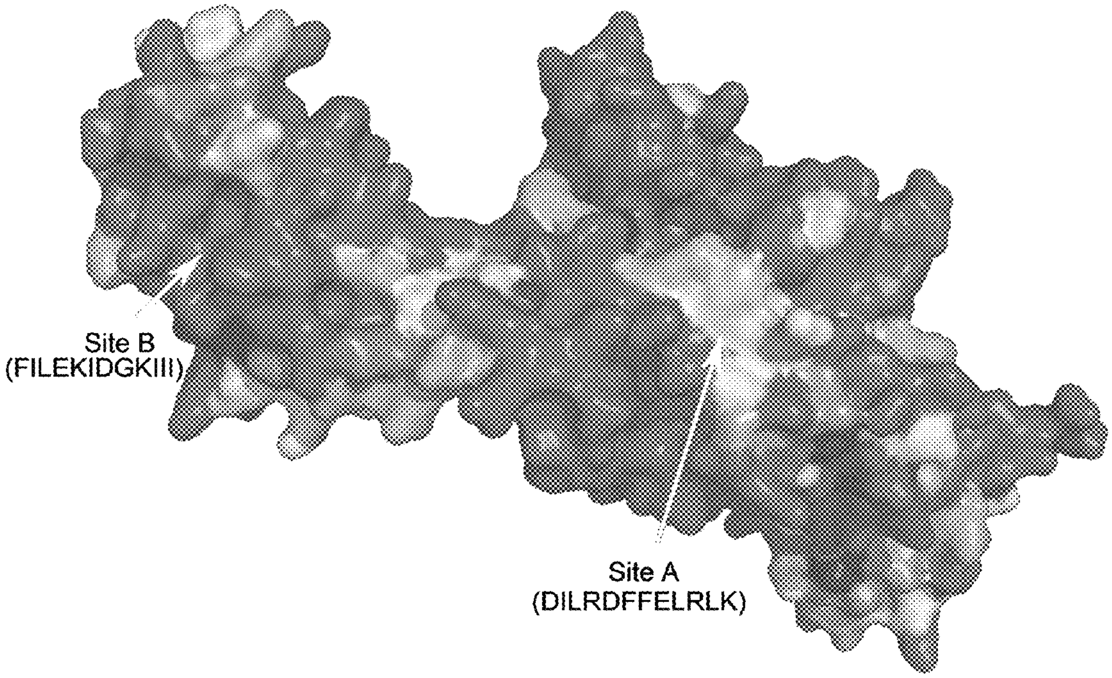
FIG. 3 is a computer image showing atomic homology model of human topoisomerase IIα generated by the program Phyre. Molecular surfaces of the homology model of human topo IIα is colored based on sequence similarity to *S. cerevisiae* topo II, calculated with clustalx and the Docker program (University of Florida, Gainesville, Fla.). Dark gray represents 100% sequence identity, and colors are graded from dark gray/light gray/medium gray which would represent no sequence identity. Nuclear export sites A(1) and B(2) were selected for high-throughput molecular docking to identify human topo IIα-specific small molecules for functional assays.
Figure 4:
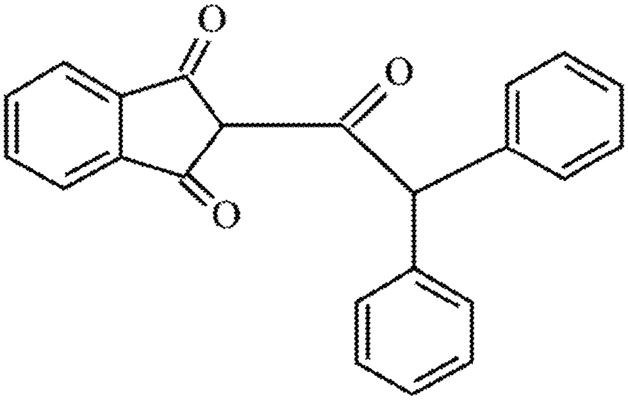
FIGS. 4(A)-(C) are illustrations of topo IIα NES inhibitors (A) NCI-9138; (B) NCI-80640; and (C) NCI-155877.
Figure 4:
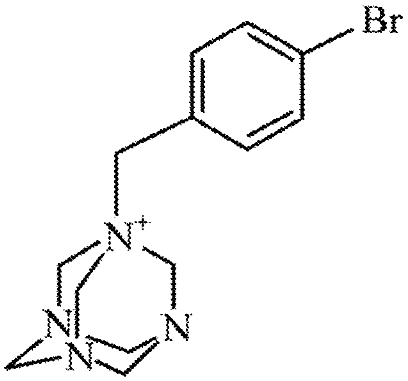
Figure 4:
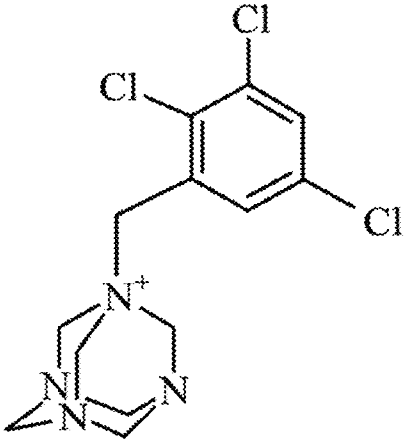
Figure 5:
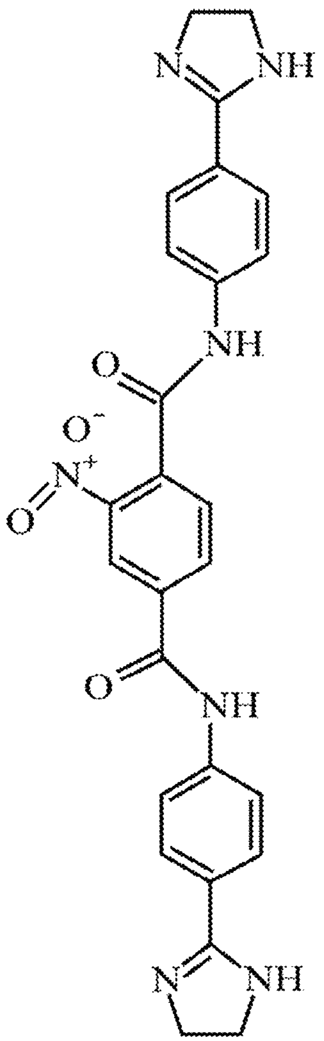
FIG. 5(A)-(D) are illustrations of topo IIα NES inhibitors (A) NCI-35847; (B) NCI-53040; (C) NCI-114057; and (D) NCI-82001.
Figure 5:
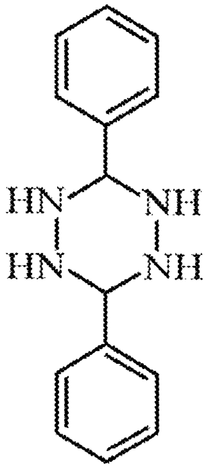
Figure 5:
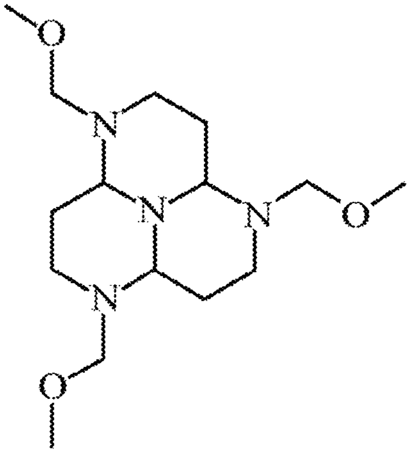
Figure 5:
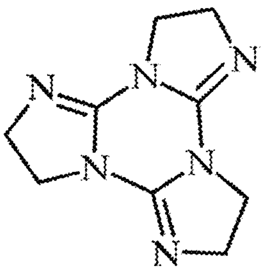

Although the crystal structure of human topo IIα has not been solved to date, the homologous *S. cerevisiae* topo II is sufficiently similar to permit generation of a high confidence atomic model of human topo IIα. Thus, the structure of *S. cerevisiae* topo II was used to create a computer generated hybrid molecule using the known three dimensional structure of yeast topo II and an atomic homology model of human topo IIα isozyme (*Homo sapiens*) (gi19913406/NP_001058.2) was generated using the Phyre Protein Fold Recognition Server (Kelley & Sternberg, Protein structure prediction on the Web: a case study using the Phyre server. Nat Protoc 2009; 4: 363-71), as seen in FIG. 2. The nuclear export sequences were mapped, as seen in FIG. 3, and these coordinates provided the basis for molecular docking. To prepare the site for docking, all water molecules were removed. Protonation of topo IIα residues was done with SYBYL (Tripos, St. Louis, Mo.) (Kelley & Sternberg, Protein structure prediction on the Web: a case study using the Phyre server. Nat Protoc 2009; 4: 363-71).

Molecules were docked in silico using atomic coordinates for each small molecule in a National Cancer Institute (NCI) small molecule database of the NCI Developmental Therapeutics Program (Driscoll, The preclinical new drug research program of the National Cancer Institute. Cancer Treat Rep 1984; 68: 63-76). 139,735 small molecules (MW<500) were positioned in each of the two selected structural pockets (hinge region outside active site) in 1,000 different orientations, with the best orientation and scores (contact and electrostatic) calculated. The scores were ranked based on predicted polar (H-bond) and nonpolar (van der Waals) interactions. The 20 highest scoring compounds for each structural pocket were obtained for in vitro assays and functional testing.

The molecular surface of the structure was explored using sets of spheres to describe potential binding pockets. The sites selected for molecular docking were defined using the SPHGEN program and filtered through the CLUSTER program (Gschwend, et al., Molecular docking towards drug discovery. J Mol Recognit 1996; 9: 175-86). Intermolecular AMBER energy scoring (van der Waals+coulombic), contact scoring, and bump filtering were implemented in DOCK v5.1.0 (Gschwend, et al., Molecular docking towards drug discovery. J Mol Recognit 1996; 9: 175-86; Ewing, et al., DOCK 4.0: search strategies for automated molecular docking of flexible molecule databases. J Comput Aided Mol Des 2001; 15: 411-28). The UCSF Chimera software package (Pettersen, et al., UCSF Chimera—a visualization system for exploratory research and analysis. J Comput Chem 2004; 25: 1605-12) was used to generate molecular graphic images. The University of Florida High-Performance Computing Center Linux cluster was used to run the docking jobs.

Four compounds were identified from the NCI database that bind to the NES of topo IIα and improve the effectiveness of topo II directed therapeutics in myeloma cells. These additional compounds were obtained from NCI based on predicted docking scores for the topo IIα NES site A.

Example 2

Compounds identified in Example 1 as the top scoring potential inhibitors for each of the two NES (20 each) were obtained from NCI and structures of these molecules confirmed using NMR and mass spectroscopy analysis, seen in FIGS. 4(A)-(C) and 5(A)-(D). The potential inhibitors were followed up using in vitro model cell cultures. MM cell lines NCI-H929 (H929) and RPMI-8226 (8226) were obtained from and tested for authenticity by the American Type Culture Collection (Manassas, Va.). All cell lines were grown as described previously (Turner, et al., Human topoisomerase IIalpha nuclear export is mediated by two CRM-1-dependent nuclear export signals. J Cell Sci 2004; 117: 3061-71).

The molecules with the highest docking scores were assayed for IC50 values. Cultures were tested for cytotoxicity using the CellTiter-Glo assay (CT-Glo cytotoxicity assay; Promega, Madison, Wis.), a luminescence-based homogeneous method for determining the number of viable cells in culture based on quantitation of the ATP present, which signals the presence of metabolically active cells (Corsino, et al., A novel class of cyclin-dependent kinase inhibitors identified by molecular docking act through a unique mechanism. J Biol Chem 2009; 284: 29945-55; Homsi, et al., Src activation in melanoma and Src inhibitors as therapeutic agents in melanoma. Melanoma Res 2009; 19: 167-75). All cells were assayed at log-phase growth conditions. Luminescence was measured with a Synergy 4 microplate reader (Bio-Tek Instruments, Inc., Winooski, Vt.). IC50 values were determined using a sigmoidal equilibrium model regression using XLfit version 5.2 (ID Business Solutions Ltd., Surrey, UK) (Corsino, et al., A novel class of cyclin-dependent kinase inhibitors identified by molecular docking act through a unique mechanism. J Biol Chem 2009; 284: 29945-55).

The IC50 values obtained from single drug cell viability assays in low-density 8226 cells revealed four lead compounds with IC50 values of 7.2±1.4 μM (NCI-35847), 12.0±4.2 μM (NCI-80640), 12.7±4.5 μM (NCI-9138), and 19.5±5.4 μM (NCI-155877), as seen in Table 1. Only NCI-9138 affected the viability of high-density cells (IC50 of 9.4 μM) as a single agent (data not shown).

TABLE 1

IC50 data.

| Cell line | NCI-35847 | NCI-80640 | NCI-9138 | NCI-155877 |
|---|---|---|---|---|
| 8226 | 7.2 (±1.7) | 12.0 (±4.2) | 12.7 (±4.5) | 19.5 (±5.4) |
| H929 | 13.9 (±1.6) | 16.2 (±3.3) | 22.2 (±4.1) | 33.6 (±4.6) |
| HL-60 | 36.5 | 11.93 | 28.31 | 20.37 |
| Kg-1a | 73.8 | 15.2 | 21.3 | 31.4 |
| MCF-7 | 68.5 | 25.9 (±0.0) | 27.2 (±1.9) | 37.1 (±7.0) |
| SK-UT | 55.3 | 25.5 (±3.5) | 29.2 (±4.9) | 50.4 (±11.3) |

TABLE 1-continued

| IC50 data. | | | | |
|---|---|---|---|---|
| Cell line | NCI-35847 | NCI-80640 | NCI-9138 | NCI-155877 |
| FLOW | 62.8 (±19.5) | 35.6 (±5.3) | 31.7 (±5.6) | 56.8 (±20.7) |
| WI-38 | 199.3 | 56.3 | 30.1 | 136 |
| PBMC | ND | 16.4 (±1.7) | 32.5 (±0.48) | 37.2 (±3.48) |

IC50 results (in μM) are shown as average ± SD.
Results were obtained from 72-h CT-Glo cytotoxicity assays.
ND, not determined.

Data from apoptosis assays indicate that three of the inhibitors (NCI-36400, NCI-35847, NCI-35024) that dock to NES site A significantly ($p<0.05$) sensitize high density MM cells to doxorubicin. CT-Glo assays determined that several of the site A inhibitors had anti-proliferative activity. CT blue (Promega Corp., Madison, Wis.) robotic cell viability assays confirmed that several of the NES site A inhibitors had anti-proliferative activity. However, none of the NES site B molecules exhibited any antineoplastic activity with or without a topo II inhibitor (data not shown).

Example 3

Figure 6:
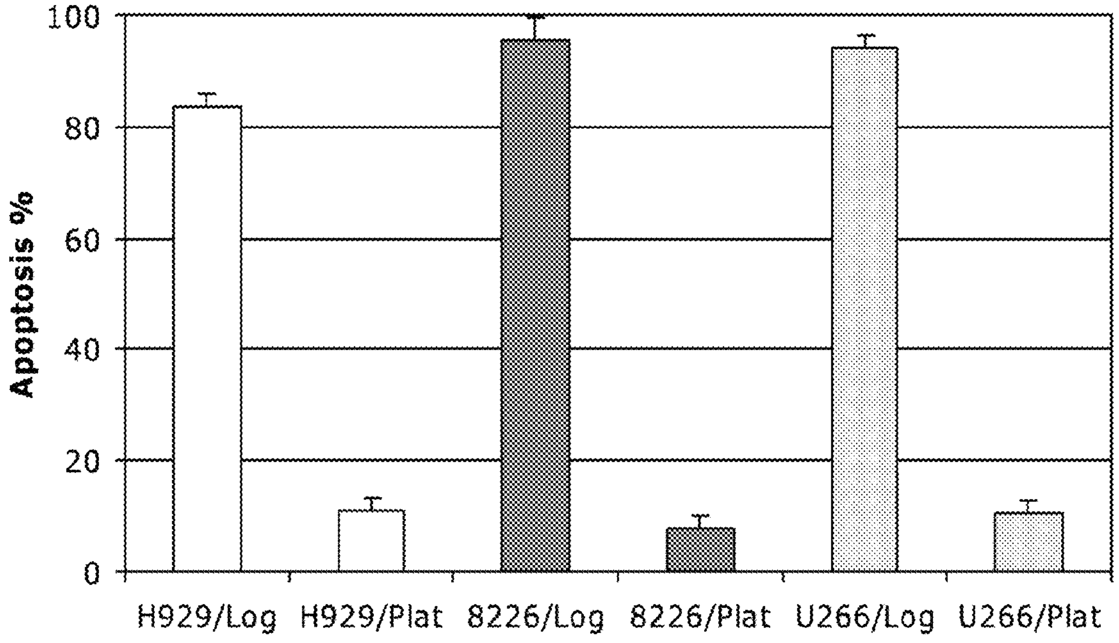
FIG. 6 is a graph showing nuclear localization of topo II sensitizes cells to doxorubicin. Human myeloma cells were grown for 16 hours at log or plateau densities, treated with 2 μM doxorubicin for 4 hours (n=2). Apoptosis was determined by caspase 3 cleavage. Cells that maintained nuclear topo IIα were more sensitive to topo IIα-targeted chemotherapy.

The compounds identified in Example 1 were tested for induction of apoptosis (cleaved caspase 3) as previously described (Turner, et al., Human multiple myeloma cells are sensitized to topoisomerase II inhibitors by CRM1 inhibition. Cancer Res 2009; 69: 6899-905). Inhibition of topo IIα export enhances DNA damaging agents, like intercalation agents such as doxorubicin. Human myeloma cells that maintained nuclear topo IIα were more sensitive to topo IIα-targeted chemotherapy in a synergistic manner, as seen in FIG. 6. As such, cells were treated with 25 μM of each identified NES compound for 20 hours followed by 4 hours with either doxorubicin (2 μM), bortezomib (10 nM), dexamethasone (10 μM), lenalidomide (10 μM), melphalan (10 μM), and topotecan (10 μM).

Figure 7:
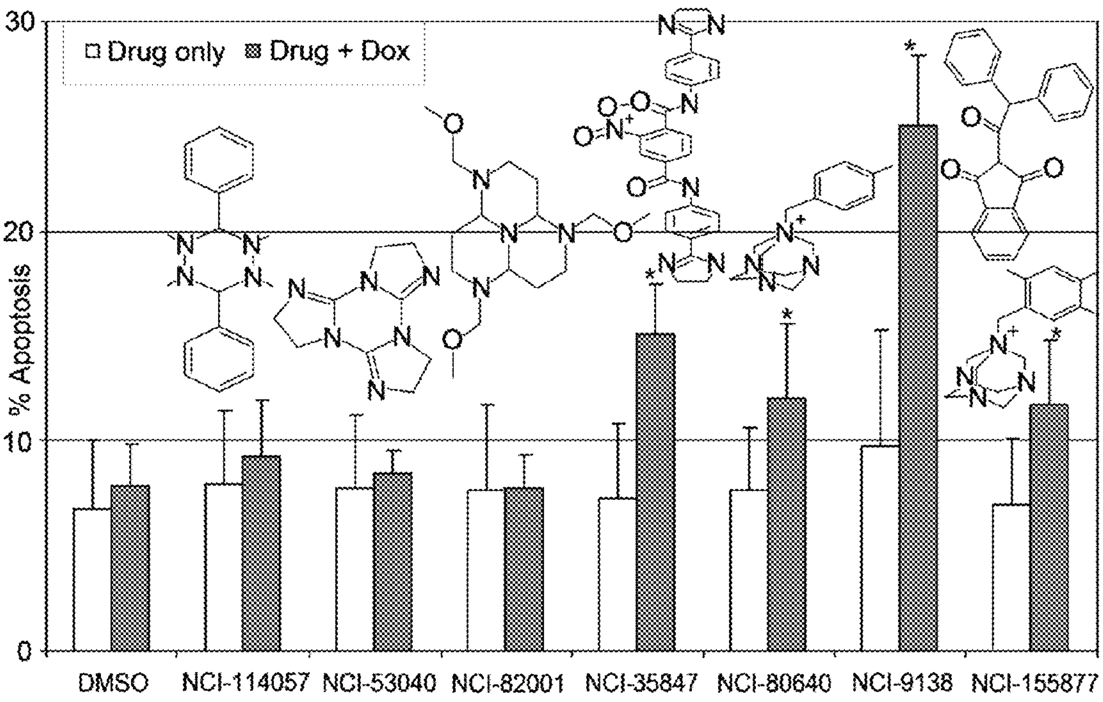
FIG. 7 is a graph overlain with compounds identified by NES docking scores. The compounds were obtained from NCI based on predicted docking scores for NES site A and site B. All compounds were further analyzed for chemical stability and structural integrity by both 1H-NMR and mass spec. After analysis of compounds, the following we were selected as the compounds that best prevented nuclear export of topo IIα in high-density drug resistant myeloma cell (H929) and synergized with the topo II inhibitor doxorubicin (2 μM) (n=4), NCI-35847, NCI-80640, NCI-9138 and NCI-15587 (25 μM) (*P<0.05).
Figure 8:
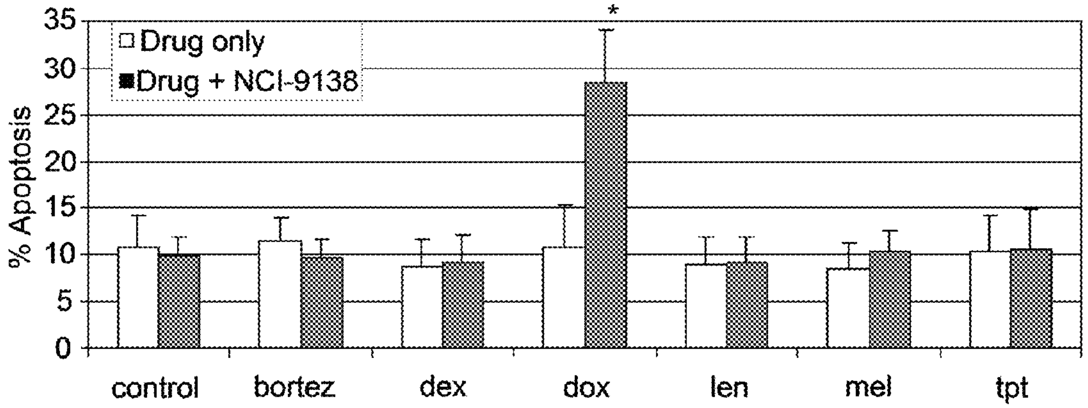
FIG. 8 is a graph showing combination effects of topo II NES inhibitors and topo II inhibitors. NCI-9138 (25 μM)

Data from caspase 3 apoptosis assays showed that the four lead compounds that dock to NES site A significantly ($P<0.05$) increased sensitivity of high-density MM cells to doxorubicin, as seen in FIG. 7. NES site A inhibitors (25 μM) alone did not induce a significant level of apoptosis versus DMSO (dimethyl sulfoxide) controls. Additionally, the most active lead compound (NCI-9138) was assayed at 25 μM with other drug combinations, including bortezomib, dexamethasone, lenalidomide, melphalan, and topotecan, as seen in FIG. 8. Tests in cells modeling AML, breast cancer and fibroblastoma show the NES site A inhibitor NCI-9138 synergized exclusively with the topo II inhibitor doxorubicin.

Lead compounds from cytotoxicity and apoptosis assays were evaluated by immunofluorescence microscopy for their effect on the intracellular location of topo IIα in treated MM cells as previous described (Turner, et al., Human multiple myeloma cells are sensitized to topoisomerase II inhibitors by CRM1 inhibition. Cancer Res 2009; 69: 6899-905). Slides were viewed with a fully automated, upright Zeiss Axio-ImagerZ.1 microscope (Carl Zeiss A G, Oberkochen, Germany). Briefly, the DAPI image was used as a mask to segment the nuclear region from the Alexa 594 image. The remaining portion of the Alexa 594 image represents the cytosol, and individual nucleus and cytosol images were analyzed.

Figure 9:
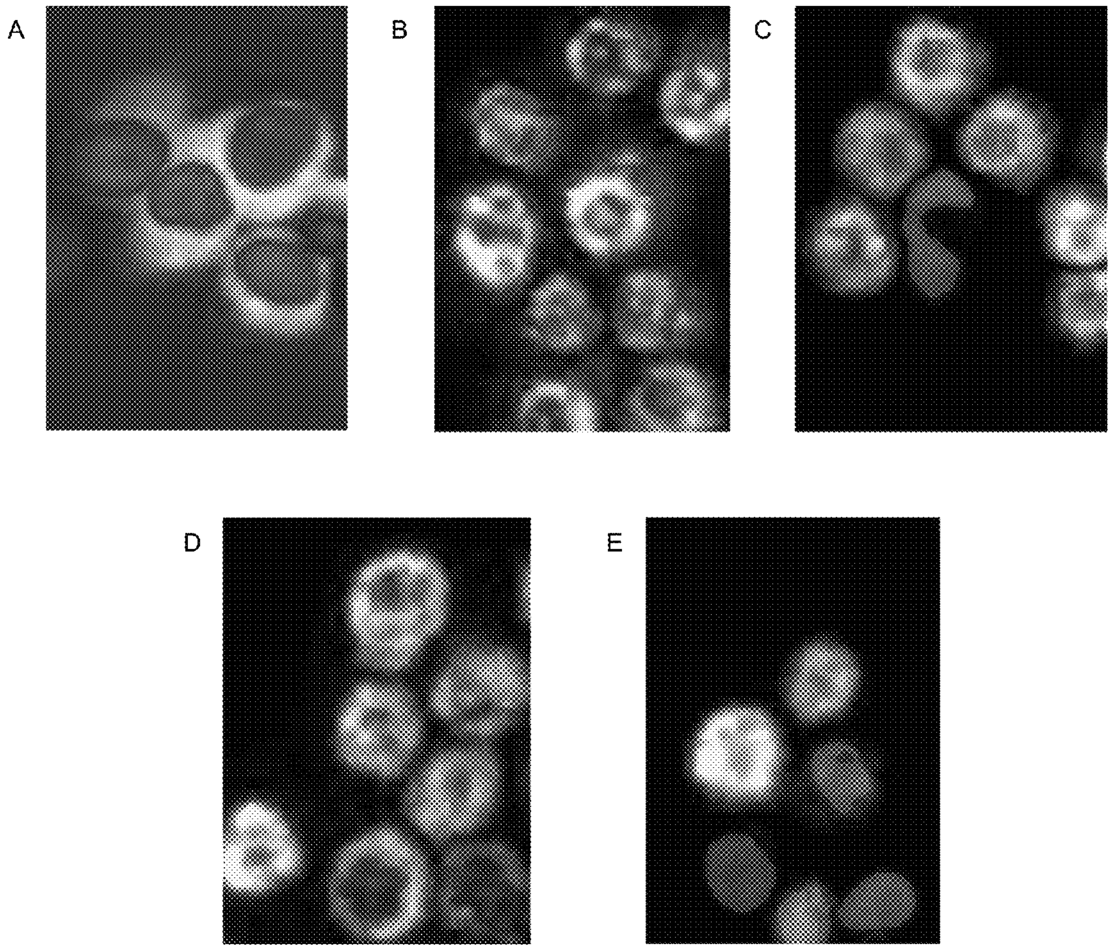
Figure 10:
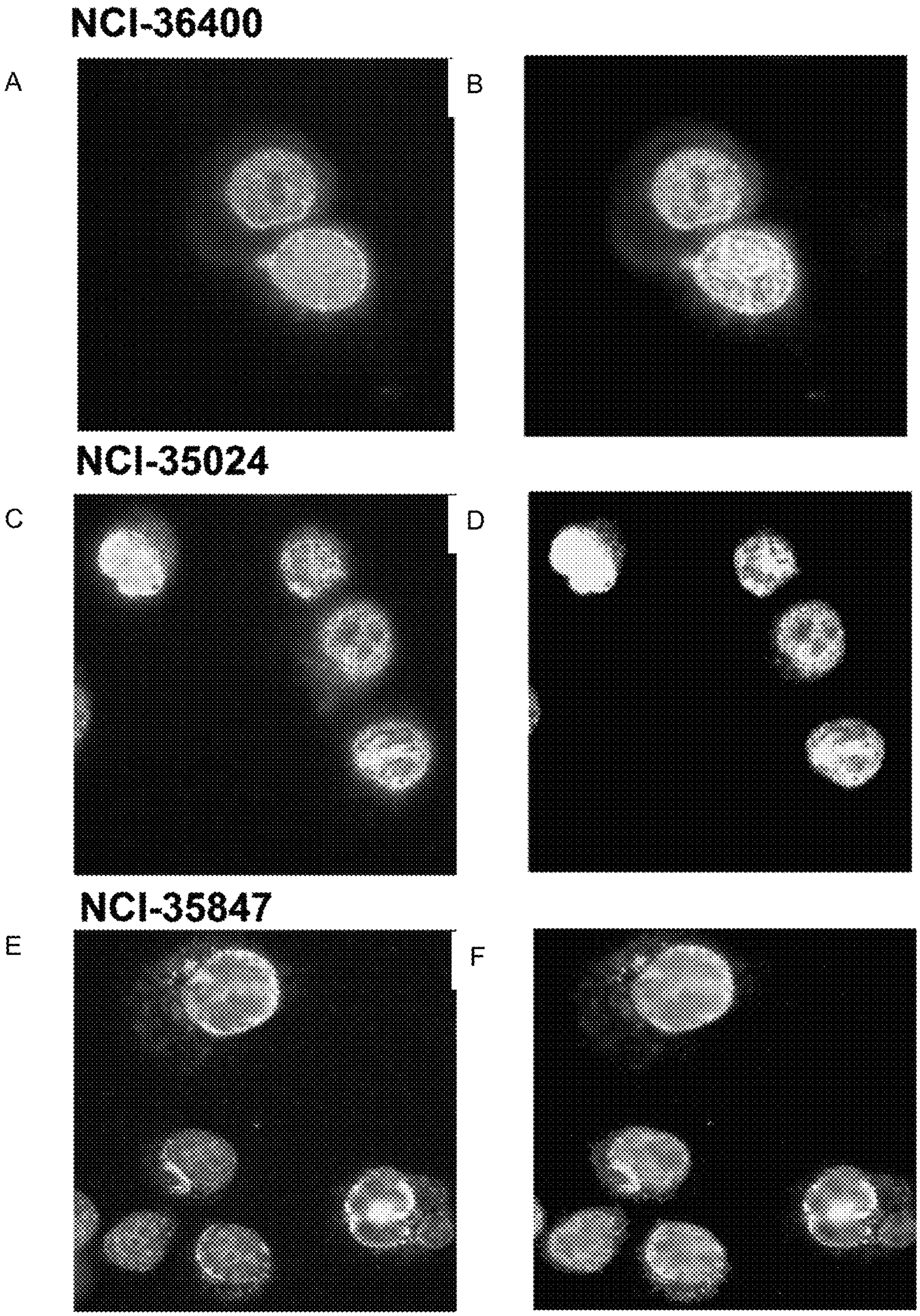

Immunofluorescence microscopy revealed a 2- to 3-fold increase in topo IIα in the cell nucleus of high-density MM cells treated for 20 hours with the four lead site A inhibitors, as seen in FIGS. 9(A)-(E). H929 cells were mock treated with 0.1% DMSO in media or with 25 μM of NES inhibitor. The high density control cells, seen in FIG. 9(A) show high levels of topo II staining outside the nucleus, evidencing export of topo II from the nucleus. However, treatment with NCI-35847, NCI-80640, NCI-9138, and NCI-155877 show overlapping staining of topo II with DAPI, as seen in FIGS. 9(B)-(E), respectively. This indicates that these NES site inhibitors prevented export of the topo II enzyme from the nucleus, consistent with the hypothesis that the NES site A docking molecules prevented nuclear export of topo IIα. Further, the NES site A inhibitors, when administered with doxorubicin, showed drug synergism, as seen in Table 2.

TABLE 2

| NES inhibitors effect on topo IIα nuclear export and synergism with doxorubicin. | | | | | |
|---|---|---|---|---|---|
| | 1 | 2 | 3 | 4 | 5 |
| NCI Compound | control | NCI-35847 | NCI-80640 | NCI-9138 | NCI-155877 |
| Molecular Weight | — | 497.5 Da | 310.2 Da | 340.4 Da | 334.7 Da |
| Docking Score | — | −50.1 kcal/mol | −48.3 kcal/mol | −47.9 kcal/mol | −46.6 kcal/mol |
| Fold-increase nuclear topo IIα* | — | 2.81 | N/A | 2.61 | 3.92 |
| Fold-Increased sensitization to dox** | — | 2.65 ± 0.90 | 2.42 ± 1.09 | 4.13 ± 1.83 | 2.82 ± 1.18 |

*Immunofluorescence microscopy, H929 human myeloma cells. Change in fluorescence intensity of topo IIα was compared in the nucleus v cytoplasm of drug-treated cells (25 μM NES inhibitor) and compared to untreated high-density controls. Nuclear and cytoplasmic fluorescence was averaged from 100-500 MM cells per drug treatment group.
**Apoptosis as measured by cleaved caspase 3 in cells treated with dox/drug (2 μM) was divided by apoptosis in cells treated with dox alone (N/A, not available).

Myeloma cells (RPMI-8226) were tested to determine if the observed effect of nuclear export inhibition of topo IIα at high-density growth conditions was due to a decrease in topo IIα protein expression. Equal numbers of cells were incubated with the lead NES (25 μM for 20 hours), and total protein was assayed by Western blot using anti-topo IIα Kis1 antibody (Millipore). Fifty micrograms of protein was loaded into each lane. GAPDH was co-assayed with topo IIα as a protein loading control (anti-GAPDH). Nuclear-cytoplasmic fractionation revealed that topo IIα NES site A docking molecules prevent nuclear export of topo IIα, as seen in FIGS. 10(A)-(F).

Lead compounds were tested for the inhibition of topo II decatenation activity with a kit purchased from TopoGen, Inc (Port Orange, Fla.) and using the protocols established by Muller (Muller, et al., Single-strand DNA cleavages by eukaryotic topoisomerase II. Biochemistry 1988; 27: 8369-79). Each drug was tested at concentrations of 25 and 50 μM, with mitoxantrone used as a control (1-10 μM). None of the NES compounds (up to 50 μM) inhibited the decatenation activity of topo II. In addition, NES inhibitors did not significantly alter total cellular levels of topo IIα in MM cells treated for 20 hours with 25 μM of each inhibitor (data not shown).

Example 4

A molecular docking model of compound NCI-9138 to the NES of topo IIα, seen in FIG. 11, indicated that inhibitors may function by preventing binding of CRM-1 signal export to leucine-rich nuclear export signals. Lead compounds identified in Example 1 were evaluated by cellular fractionation to confirm whether they prevented nuclear export of topo IIα. Human myeloma cells were placed at plateau concentrations ($4\times10^6$ cells/ml), and NES inhibitors were added at 25 μM for 20 hours. Cells were collected, washed in PBS, and fractionated by a method adapted from Li et al. (Li Y, Bor Y C, Misawa Y, Xue Y, Rekosh D, Hammarskjold M L. An intron with a constitutive transport element is retained in a Tap messenger RNA. Nature 2006; 443: 234-7). Separated fractions containing nuclei or precipitated cytosol were dissolved in 2% SDS buffer and assayed by SDS-PAGE Western blot analysis. Blots were probed with an anti-topo IIα Kis1 antibody (Millipore Corp.). Lead compounds were also tested to determine if nuclear export inhibition was specific to topo IIα protein. Cells grown at log-phase concentrations were also fractionated. After MM cells were treated with NCI-9138 at 25 μM for 20 hours, CRM1-topo IIα complexes were isolated from cells by immunoprecipitation using a combination of both protein A and protein G magnetic beads according to the manufacturer's protocol (Miltenyi Biotec, Cologne, Germany). Co-immunoprecipitation was performed with 2 μg of anti-CRM1 antibody (Santa Cruz Biotechnology, Inc., Santa Cruz, Calif.). Immunoprecipitation samples were separated by SDS-PAGE, transferred to nitrocellulose membranes, and probed with anti-topo IIα Kis1 antibody (Millipore, Corp., Billerica, Mass.) and anti-mouse horseradish peroxidase secondary antibody.

Co-immunoprecipitation of topo IIα with a CRM1 antibody and subsequent Western blot analysis showed that topo IIα was prevented from binding to CRM1 by the NES inhibitor NCI-9138, as seen in FIG. 12. Western blot analysis of nuclear and cytoplasmic fractions confirmed that the lead NES compounds increased nuclear localization of topo IIα. In human myeloma RPMI-H929 cells, the addition of compounds NCI-35847, NCI-80640, and NCI-9138 (100 μM, 24 hours) reduced cytoplasmic levels of topo IIα equivalent to that produced by the CRM-1 inhibitor ratjadone C, seen in FIGS. 13(A) and (B). However, compound NCI-155877 did not significantly reduce the level of cytoplasmic topo IIα relative to untreated controls. NCI-32237, a control compound did not affect nuclear export of topo II, confirming that the inhibitors likely function through NES inhibition.

Nuclear fractions of low-density myeloma cells (H929) were assayed for p53 to determine if nuclear export inhibition was specific to topo IIα protein, as seen in FIG. 14. p53 is known to undergo nuclear to cytoplasmic shuttling in logarithmically growing myeloma cells and therefore was used to test the whether nuclear export was topo IIα specific. p53 was exported from the nucleus to the cytoplasm in myeloma cells cultured at low concentrations ($2\times10^5$/mL). Cells grown at low concentrations were treated with the lead NES inhibitors (25 μM) or a leptomycin B (5 nM) control for 20 hours and chemically fractionated. Nuclei were assayed by SDS-PAGE Western blot analysis for p53 protein. NCI compounds 35847, 9138, and 155877 did not prevent export of p53, indicating that these compounds may specifically inhibit topo IIα export, as seen in FIG. 14. Interestingly, NCI-80640 was found to significantly inhibit nuclear export of p53, indicating that this drug can affect transport of other nuclear proteins into the cytoplasm.

Example 5

Additional cancer and normal cell lines were assayed to determine whether inhibition of topo IIα nuclear export sensitized these cell lines to the topo II inhibitor, doxorubicin. Cell cultures were continuously treated with NES inhibitors (25 μM) for 24 hours. Doxorubicin was added to a final concentration of 2 μM during the final 4 h of treatment and then apoptosis was measured by cleaved caspase 3 antibody staining (Cell Signaling Technology, Beverly, Mass.) and flow cytometry. Apoptosis was measured by cleaved caspase 3 antibody staining (Cell Signaling Technology) and flow cytometry. Cells lines assayed included normal fibroblasts WI-38 (American Type Culture Collection, Manassas, Va.) and Flow 2000 (Flow Laboratories, Inc., Rockville, Md.) peripheral blood mononuclear cells (PBMCs) from normal donors (Florida Blood Services, St. Petersburg, Fla.), MCF7 breast cancer cells (American Type Culture Collection), and acute myeloid leukemia (AML) cell lines HL-60 and KG1a (American Type Culture Collection). Volunteer donors to Florida Blood Services provided informed consent to allow the use of their cells in accordance with the Declaration of Helsinki.

High-density cultures of normal fibroblasts WI-38 and Flow 2000, seen in FIGS. 15 and 16, and normal PBMCs and AML cells HL-60 and KG1a, seen in FIGS. 17-19, were not sensitized to doxorubicin. However, the breast cancer cell line MCF7, seen in FIG. 20, was sensitive to NES inhibitors and doxorubicin. In contrast to MM cells, topo IIα does not preferentially localize to the cytoplasm of MCF7 cells under high-density growth conditions (unpublished data). The present combination shows high specificity to MM, as promyelocytic leukemia, myeloblastic leukemia, and normal fibroblast models do not sensitize to topo II NES inhibitors or combinations of to topo II NES inhibitors and topo II inhibitors.

TABLE 3

Additional compounds identified as topoisomerase II nuclear export signal inhibitors.

| NCI-203305 CID: 4003104 | 1-bromo-15,3,5,7-tetraazatricyclo[3.3.1.1~3.7~] decane (ACD/Name 4.0) | NCI-281703 CID: 430738 | N-isobutyl-1,3,5-triazatricyclo[3.3.1.1~3,7~] decan-7-amine (ACD/Name 4.0) |
|---|---|---|---|
| Docking score | −42.3161 | Docking score | −42.1261 |

TABLE 3-continued

| Additional compounds identified as topoisomerase II nuclear export signal inhibitors. | | | |
|---|---|---|---|
| NCI-203305<br>CID: 4003104 | 1-bromo-15,3,5,7-tetraazatricyclo[3.3.1.1~3.7~]decane (ACD/Name 4.0) | NCI-281703<br>CID: 430738 | N-isobutyl-1,3,5-triazatricyclo[3.3.1.1~3,7~]decan-7-amine (ACD/Name 4.0) |
| VDW | −7.03116 | VDW | −13.8052 |
| ES | −35.285 | ES | −28.3209 |
| MW | 220.0916 | MW | 210.3216 |
| Formula | $C_6H_{12}BrN_4$ | Formula | $C_{11}H_{22}N_4$ |
| HDonors | 0 | HDonors | 1 |
| HAcceptors | 3 | HAcceptors | 4 |
| Active pass screen ($p < 0.05$) | Bisphosphonate: 0.029<br>Ribonucleoside diphosphate reductase inhibitor: 0.041 | Active pass screen ($p < 0.05$) | Carbonic anhydrase inhibitor: 0.043 |
| Active pass screen ($p < 0.05$) | Anesthetic inhalation: 0.0080<br>Mutagenic: 0.0060 | Active pass screen ($p < 0.05$) | Antiviral: 0.0080<br>Carbonic anhydrase inhibitor: 0.0080 |

TABLE 4

| A list of identified topoisomerase II nuclear export signal inhibitors. | | |
|---|---|---|
| Compound Name/<br>Chemical Formula/<br>Molecular Weight/<br>NCI Number | Structure | Docking Score |
| 3,6-diphenyl-1,2,4,5-tetraazinane<br>(ACD/Name 4.0)<br>C14H16N4<br>240.3072<br>NCI-114057 | 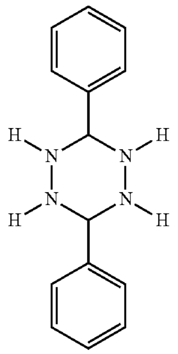 [SMILES: c1ccc(C2NNC(c3ccccc3)NN2)cc1] | −58.05567932 |
| 3,6-dibutyl-1,2,4,5-tetraazinane<br>(ACD/Name 4.0)<br>C10H24N4<br>200.3264<br>NCI-254980 | 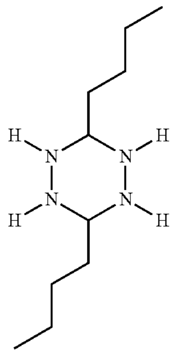 | −56.0453949 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 1-(2-naphthyl)-2-(15,3,5,7-tetraazatricyclo[3.3.1.1~3,7~]dec-1-yl)ethanone (ACD/Name 4.0) C18H21N4O 309.3901 NCI-36400 | 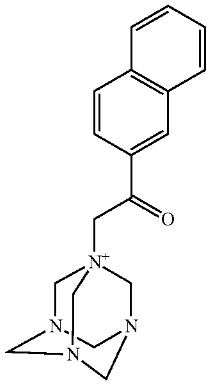 [SMILES: O=C(C[N+]12CN3CN(CN(C3)C1)C2)c1ccc2ccccc2c1] | −52.10803223 |
| 2,3,6,7,10,11-hexahydrotriimidazo[1,2-a:1,2-c:1,2-e][1,3,5]triazine (ACD/Name 4.0) C9H12N6 204.234 NCI-53040 | 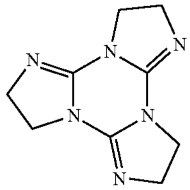 [SMILES: C1CN2C(=N1)N1CCN=C1N1CCN=C21] | −51.23078156 |
| 1,4,7-tris(methoxymethyl)dodecahydro-1,4,7,9b-tetraazaphenalene (ACD/Name 4.0) C15H30N4O3 314.427 NCI-82001 | 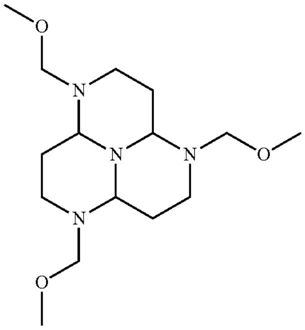 | −50.65611267 |
| 2,5,8-trimethyldodecahydro-1,4,7,9b-tetraazaphenalene (ACD/Name 4.0) C12H24N4 224.3484 NCI-218332 | 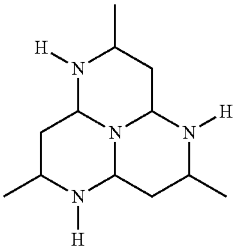 | −50.59078217 |
| 1-phenyl-2-(15,3,5,7-tetraazatricyclo[3.3.1.1~3,7~]dec-1-yl)ethanone (ACD/Name 4.0) C14H19N4O 259.3303 NCI-35721 | 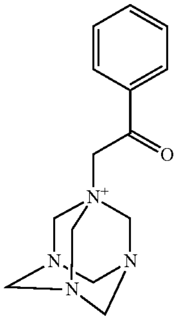 [SMILES: O=C(C[N+]12CN3CN(CN(C3)C1)C2)c1ccccc1] | −50.40135956 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| N1,N4-bis(4-(4,5-dihydro-1H-imidazol-2-yl)phenyl)-2-(hydroxy(oxido)amino)terephthalamide (ACD/Name 4.0) C26H23N7O4 497.5122 NCI-35847 | 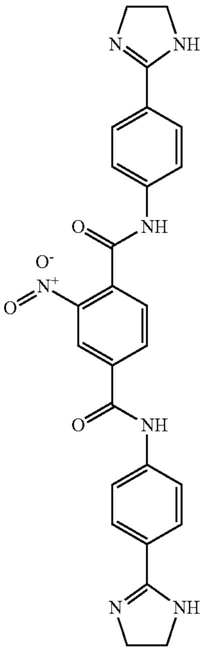 | −50.12254715 |
| ethyl 3-((2-chloro-5-(hydroxy(oxido)amino)-6-methylhexahydro-4-pyrimidinyl)amino)propanoate (ACD/Name 4.0) C10H19ClN4O4 294.7375 NCI-134514 | 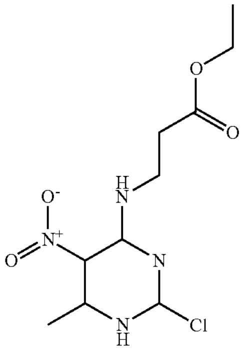 [SMILES: CCOC(=O)CCNC1NC(Cl)NC(C)C1[N+](=O)[O-]] | −49.70521545 |
| 2-(15,3,5,7-tetraazatricyclo[3.3.1.1~3,7~]dec-1-yl)-1-(5,6,7,8-tetrahydro-2-naphthalenyl)ethanone (ACD/Name 4.0) C18H25N4O 313.4217 NCI-36791 | 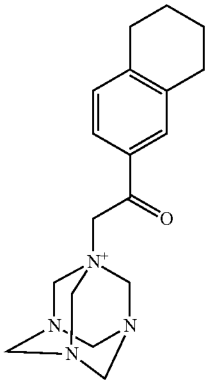 [SMILES: O=C(C[N+]12CN3CN(CN(C3)C1)C2)c1ccc2c(c1)CCCC2] | −49.56581497 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| 2,5,8-trimethyldodecahydro-1,4,7,9b-tetraazaphenalene (ACD/Name 4.0) C12H24N4 224.3484 NCI-218332 | 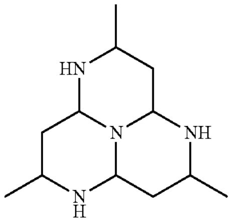 | −49.42612457 |
| 1-(4-iodophenyl)-2-(15,3,5,7-tetraazatricyclo[3.3.1.1~3,7~]dec-1-yl)ethanone oxime (ACD/Name 4.0) C14H19IN5O 400.2415 NCI-35024 | 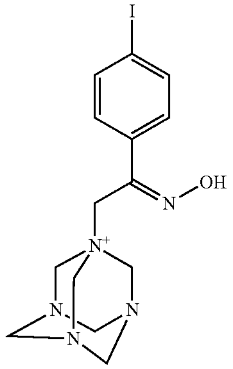 [SMILES: O/N=C(/C[N+]12CN3CN(CN(C3)C1)C2)c1ccc(I)cc1] | −49.32891846 |
| ethyl 3-((2-chloro-5-(hydroxy(oxido)amino)-6-methylhexahydro-4-pyrimidinyl)amino)propanoate (ACD/Name 4.0) C10H19ClN4O4 294.7375 NCI-134514 | 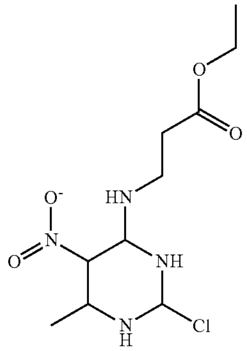 | −48.98755646 |
| methyl 4-(15,3,5,7-tetraazatricyclo[3.3.1.1~3,7~]dec-1-ylmethyl)phenyl sulfone (ACD/Name 4.0) C14H21N4O2S 309.4055 NCI-371729 | 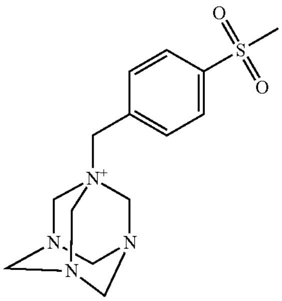 [SMILES: CS(=O)(=O)c1ccc(C[N+]23CN4CN(CN(C4)C2)C3)cc1] | −48.88472748 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| N1,N2-bis(2-(1-piperazinyl)ethyl)ethanedithioamide (ACD/Name 4.0) C14H28N6S2 344.5354 NCI-50077 | 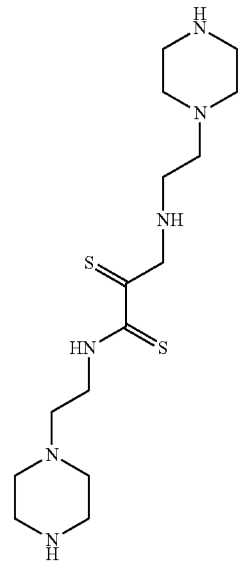 [SMILES: S=C(CNCCN1CCNCC1)C(=S)NCCN1CCNCC1] | −48.71514893 |
| 1-(4-bromobenzyl)-15,3,5,7-tetraazatricyclo[3.3.1.1~3,7~]decane (ACD/Name 4.0) C13H18BrN4 310.216 NCI-80640 | 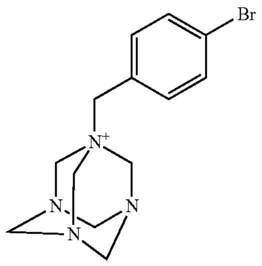 [SMILES: Brc1ccc(C[N+]23CN4CN(CN(C4)C2)C3)cc1] | −48.63881683 |
| 1-(4-chlorophenyl)-2-(15,3,5,7-tetraazatricyclo[3.3.1.1~3,7~]dec-1-yl)ethanone (ACD/Name 4.0) C14H18ClN4O 293.7754 NCI-32895 | 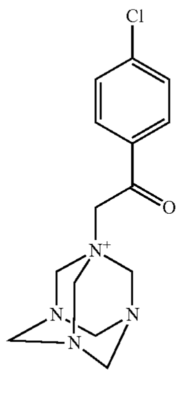 [SMILES: O=C(C[N+]12CN3CN(CN(C3)C1)C2)c1ccc(Cl)cc1] | −48.02495956 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| 1-[1,1'-biphenyl]-4-yl-2-(15,3,5,7-tetraazatricyclo[3.3.1.1~3,7~]dec-1-yl)ethanone (ACD/Name 4.0)<br>C20H23N4O<br>335.4279<br>NCI-35450 | 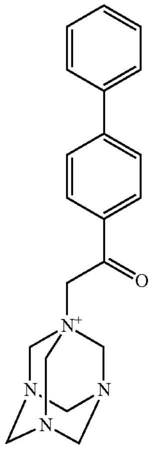 [SMILES: O=C(C[N+]12CN3CN(CN(C3)C1)C2)c1ccc(-c2ccccc2)cc1] | −47.98036575 |
| 1-(4-methoxyphenyl)-2-(15,3,5,7-tetraazatricyclo[3.3.1.1~3,7~]dec-1-yl)ethanone (ACD/Name 4.0)<br>C15H21N4O2<br>289.3565<br>NCI-34740 | 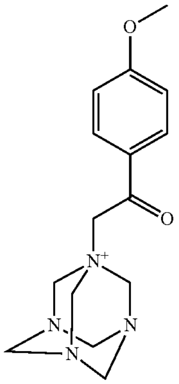 [SMILES: COc1ccc(C(=O)C[N+]23CN4CN(CN(C4)C2)C3)cc1] | −47.92876816 |
| 2-(diphenylacetyl)-1H-indene-1,3(2H)-dione (ACD/Name 4.0)<br>C23H16O3<br>340.3776<br>NCI-9138 | 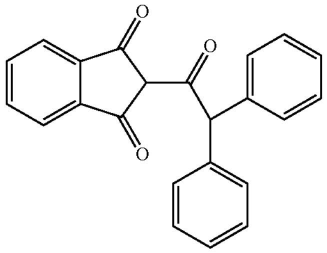 [SMILES: O=C1c2ccccc2C(=O)C1C(=O)C(c1ccccc1)c1ccccc1] | −47.87641907 |
| 2,4,6-tribenzyl-1,3,5-triazabicyclo[3.1.0]hexane (ACD/Name 4.0)<br>C24H25N3<br>355.4816<br>NCI-281706 | 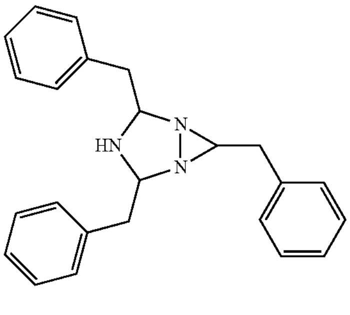 [SMILES: c1ccc(CC2NC(Cc3ccccc3)N3C(Cc4ccccc4)N23)cc1] | −47.77204895 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| 4-(3-methoxybenzyl)-1-piperazinamine (ACD/Name 4.0) C12H19N3O 221.3016 NCI-239384 | 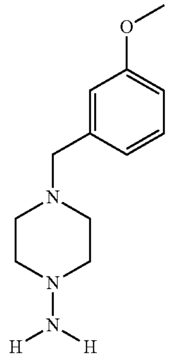 [SMILES: COc1cccc(CN2CCN(N)CC2)c1] | −47.74377441 |
| 4-(4-methoxybenzyl)-2,6-dimethyl-1-piperazinamine (ACD/Name 4.0) C14H23N3O 249.3552 NCI-212556 | 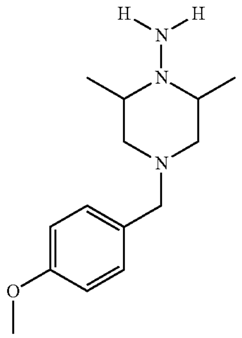 [SMILES: COc1ccc(CN2CC(C)N(N)C(C)C2)cc1] | −47.70429993 |
| 1-(4-(hydroxy(oxido)amino)benzyl)-3,5-dimethyl-1,3,5-triazinane (ACD/Name 4.0) C12H18N4O2 250.2998 NCI-351295 | 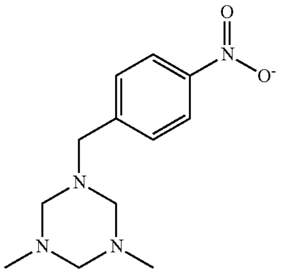 | −47.55976486 |
| 1-(3-hydrazinopropyl)-4-methylpiperazine (ACD/Name 4.0) C8H20N4 172.2728 NCI-356363 | 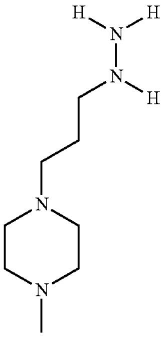 | −47.19536209 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| 4-(4-methoxybenzyl)-2,6-dimethyl-1-piperazinamine (ACD/Name 4.0) C14H23N3O 249.3552 NCI-212556 | 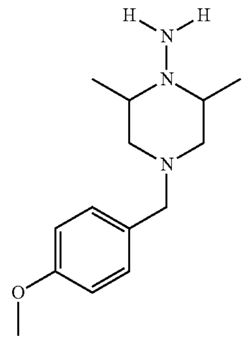 [SMILES: COc1ccc(CN2CC(C)N(N)C(C)C2)cc1] | −47.18786621 |
| 1,4,7-tris(methoxymethyl)dodecahydro-1,4,7,9b-tetraazaphenalene (ACD/Name 4.0) C15H30N4O3 314.427 NCI-82001 | 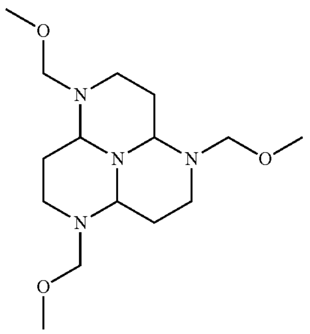 | −47.11424255 |
| ethyl 3-((2-chloro-5-(hydroxy(oxido)amino)-6-methylhexahydro-4-pyrimidinyl)amino)propanoate (ACD/Name 4.0) C10H19ClN4O4 294.7375 NCI-134514 | 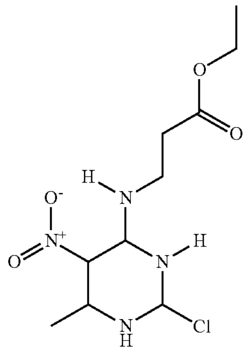 [SMILES: CCOC(=O)CCNC1NC(Cl)NC(C)C1[N+](=O)[O-]] | −47.07342529 |
| 1-(4-bromophenyl)-2-(15,3,5,7-tetraazatricyclo[3.3.1.1~3,7~]dec-1-yl)ethanone (ACD/Name 4.0) C14H18BrN4O 338.2264 NCI-32237 | 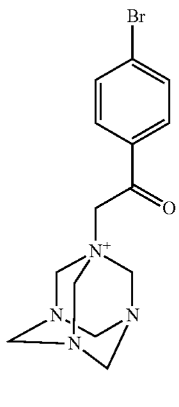 [SMILES: O=C(C[N+]12CN3CN(CN(C3)C1)C2)c1ccc(Br)cc1] | −47.07016373 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 1-(2,4,5-trichlorobenzyl)-15,3,5,7-tetraazatricyclo[3.3.1.1~3,7~]decane (ACD/Name 4.0)<br>C13H16Cl3N4<br>334.6552<br>NCI-155877 | 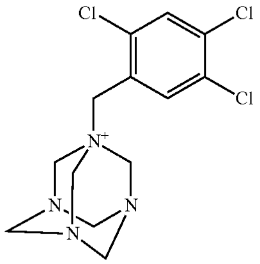 [SMILES: Clc1cc(Cl)c(C[N+]23CN4CN(CN(C4)C2)C3)cc1Cl] | −46.60263824 |
| 1-(4-iodophenyl)-2-(15,3,5,7-tetraazatricyclo[3.3.1.1~3,7~]dec-1-yl)ethanone (ACD/Name 4.0)<br>C14H18IN4O<br>385.2269<br>NCI-34564 | 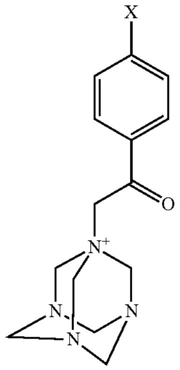 | −46.51460648 |
| 1,3,5-tricyclohexyl-1,3,5-triazinane (ACD/Name 4.0)<br>C21H39N3<br>333.5592<br>NCI-6441 | 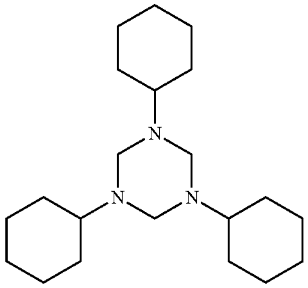 [SMILES: C1CCC(N2CN(C3CCCCC3)CN(C3CCCCC3)C2)CC1] | −46.50683975 |
| 1-(1,3-benzodioxol-5-yl(1-piperazinyl)methyl)piperazine (ACD/Name 4.0)<br>C16H24N4O2<br>304.3912<br>NCI-87015 | 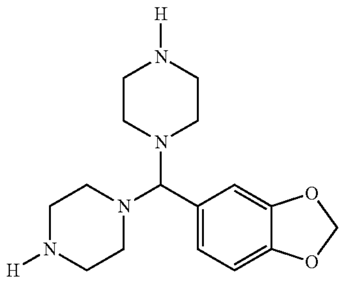 [SMILES: c1cc2c(cc1C(N1CCNCC1)N1CCNCC1)OCO2] | −46.46583557 |
| N-butyl-N-methyl-1,3,5-triazatricyclo[3.3.1.1~3,7~]decan-7-amine (ACD/Name 4.0)<br>C12H24N4<br>224.3484<br>NCI-281702 | 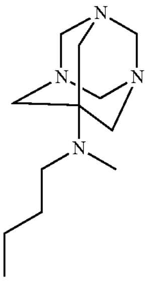 [SMILES: CCCCN(C)C12CN3CN(CN(C3)C1)C2] | −46.4388504 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 1-((4-methoxyphenyl)(1-piperazinyl)methyl)piperazine (ACD/Name 4.0) C16H26N4O 290.4076 NCI-87062 | 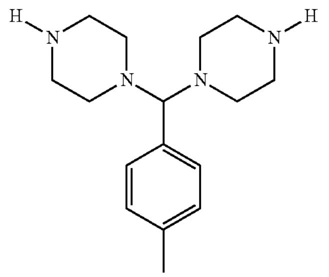 [SMILES: Cc1ccc(C(N2CCNCC2)N2CCNCC2)cc1] | −46.23457718 |
| 1-(2,4-dichlorophenyl)-2-(15,3,5,7-tetraazatricyclo[3.3.1.1~3,7~]dec-1-yl)ethanone (ACD/Name 4.0) C14H17Cl2N4O 328.2205 NCI-33450 | 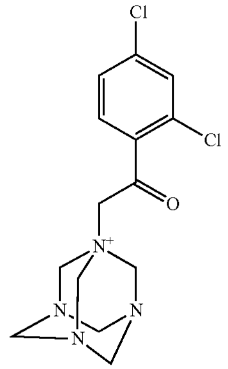 [SMILES: O=C(C[N+]12CN3CN(CN(C3)C1)C2)c1ccc(Cl)cc1Cl] | −46.07444763 |
| 1,4,8,11-tetraazatricyclo [9.3.1.1~4,8~]hexadecane (ACD/Name 4.0) C12H24N4 224.3484 NCI-358063 | 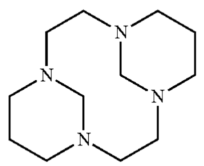 [SMILES: C1CN2CCN3CCCN(CCN(C1)C2)C3] | −46.06830597 |
| 2-(1-piperazinyl)-N-(2-pyridinylmethyl)ethanamine (ACD/Name 4.0) C12H20N4 220.3168 NCI-66183 | 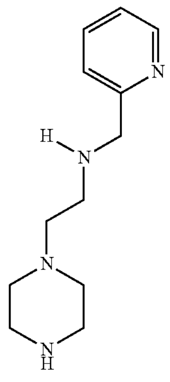 [SMILES: c1ccc(CNCCN2CCNCC2)nc1] | −46.03097534 |

TABLE 4-continued
| A list of identified topoisomerase II nuclear export signal inhibitors. | | |
|---|---|---|
| Compound Name/ Chemical Formula/ Molecular Weight/ NCI Number | Structure | Docking Score |
| 1-(4-iodophenyl)-2-(15,3,5,7-tetraazatricyclo[3.3.1.1~3,7~]dec-1-yl)ethanone oxime (ACD/Name 4.0) C14H19IN5O 400.2415 NCI-35024 | 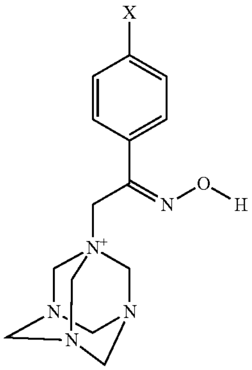 | −45.93972778 |
| Prospidin C18H36Cl2N4O2 411.414 NCI-166100 | 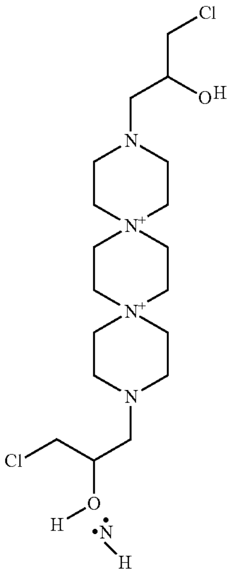 | −45.83865356 |
| Prospidin C18H36Cl2N4O2 411.414 NCI-166100 | 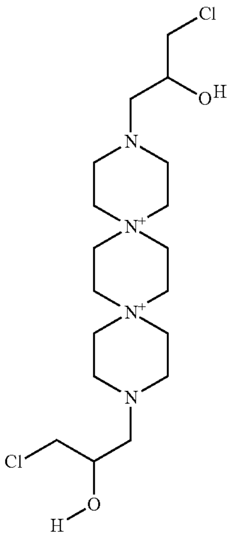 | −45.81716537 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 1,4-bis(1H-imidazol-2-ylmethyl)piperazine (ACD/Name 4.0) C12H18N6 246.3144 NCI-116533 | 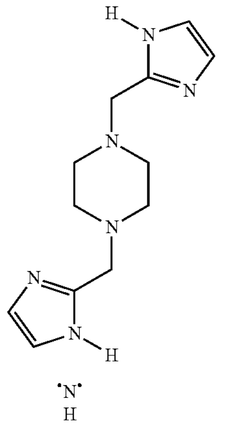 [SMILES: c1c[nH]c(CN2CCN(Cc3ncc[nH]3)CC2)n1] | −45.74671173 |
| ethyl 3-((2-chloro-5-(hydroxy(oxido)amino)-6-methylhexahydro-4-pyrimidinyl)amino)propanoate (ACD/Name 4.0) C10H19ClN4O4 294.7375 NCI-134514 | 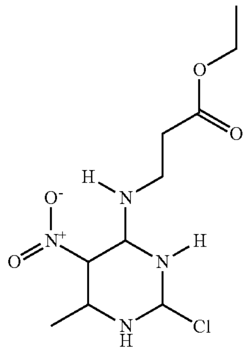 [SMILES: CCOC(=O)CCNC1NC(Cl)NC(C)C1[N+](=O)[O-]] | −45.73298645 |
| N-methyl-N-pentyl-1,3,5-triazatricyclo[3.3.1.1~3.7~]decan-7-amine (ACD/Name 4.0) C13H26N4 238.3752 NCI-281708 | 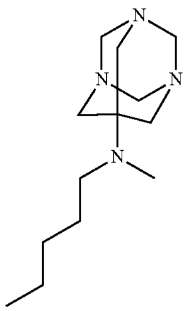 [SMILES: CCCCCN(C)C12CN3CN(CN(C3)C1)C2] | −45.71780396 |
| 1,3,5-triisopropyl-1,3,5-triazinane (ACD/Name 4.0) C12H27N3 213.3654 NCI-166334 | 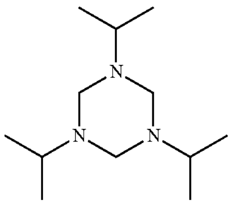 | −45.68099976 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 1-methyl-4-(2-((2-(4-methyl-1-piperazinyl)ethyl)dithio)ethyl)piperazine (ACD/Name 4.0)<br>C14H30N4S2<br>318.5378<br>NCI-149852 | 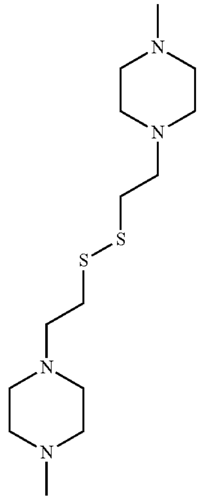 [SMILES: CN1CCN(CCSSCCN2CCN(C)CC2)CC1] | −45.64836121 |
| Glycine, N,N'-1,2-ethanediylbis(N-carboxymethyl)-,N,N:N',N'-diimide<br>C10H14N4O4<br>254.245<br>NCI-129942 | 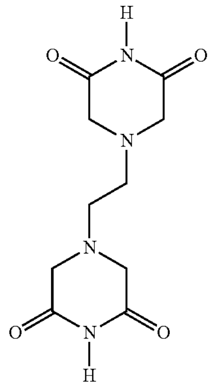 [SMILES: O=C1CN(CCN2CC(=O)NC(=O)C2)CC(=O)N1] | −45.63679504 |
| 1-(3-methyl-2-butenyl)-15,3,5,7-tetraazatricyclo[3.3.1.1~3,7~]decane (ACD/Name 4.0)<br>C11H21N4<br>209.3137<br>NCI-508350 | 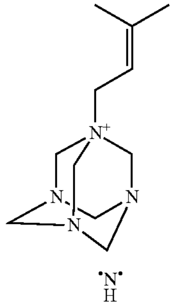 | −45.59712601 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 1-(4-isobutylbenzyl)-15,3,5,7-tetraazatricyclo[3.3.1.1~3,7~]decane (ACD/Name 4.0) C17H27N4 287.4271 NCI-118977 | 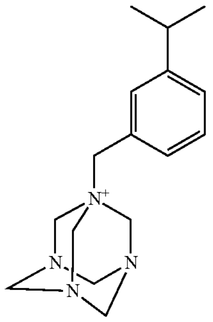 [SMILES: CC(C)c1cccc(C[N+]23CN4CN(CN(C4)C2)C3)c1] | −45.49806213 |
| 3-(4-(3-(1-aziridinyl)propyl)-1-piperazinyl)propylamine (ACD/Name 4.0) C12H26N4 226.3642 NCI-101261 | 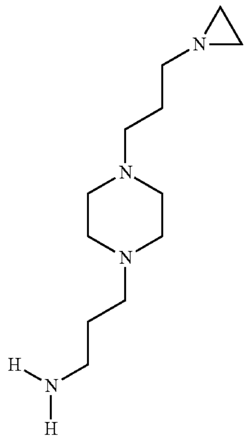 [SMILES: NCCCN1CCN(CCCN2CC2)CC1] | −45.49415588 |
| 4-benzyl-1,4-diazepan-1-amine (ACD/Name 4.0) C12H19N3 205.3022 NCI-21235 | 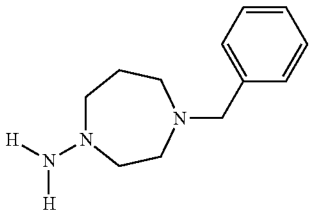 [SMILES: NN1CCCN(Cc2ccccc2)CC1] | −45.38274384 |
| tetradecahydro-2,3-phenazinediamine (ACD/Name 4.0) C12H24N4 224.3484 NCI-667746 | 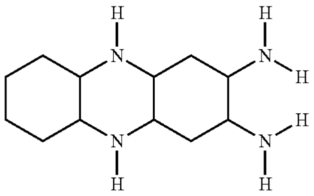 [SMILES: NC1CC2NC3CCCCC3NC2CC1N] | −45.21557617 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 2-(1-piperazinyl)-N-(3-pyridinylmethyl)ethanamine (ACD/Name 4.0)<br>C12H20N4<br>220.3168<br>NCI-66184 | 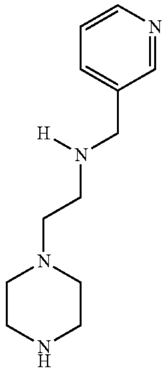 [SMILES: c1cncc(CNCCN2CCNCC2)c1] | −45.08872223 |
| 1-(7-methyl-8-(3,4,5-trimethoxyphenyl)-7,8-dihydro-6H-[1,3]dioxolo[4,5-g]chromen-6-yl)hydrazine (ACD/Name 4.0)<br>C20H24N2O6<br>388.4194<br>NCI-667918 | 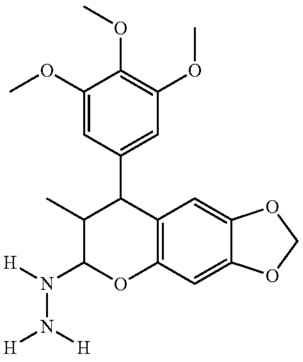 [SMILES: COc1cc(C2c3cc4c(cc3OC(NN)C2C)OCO4)cc(OC)c1OC] | −45.02167511 |
| 5-(15,3,5,7-tetraazatricyclo[3.3.1.1~3,7~]dec-1-yl)pentanenitrile (ACD/Name 4.0)<br>C11H20N5<br>222.3125<br>NCI-131869 | 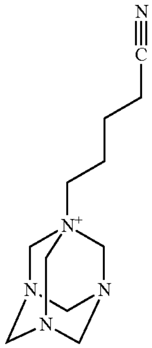 [SMILES: N#CCCCC[N+]12CN3CN(CN(C3)C1)C2] | −44.85451126 |
| 1-(1-naphthyl)-2-(15,3,5,7-tetraazatricyclo[3.3.1.1~3,7~]dec-1-yl)ethanone (ACD/Name 4.0)<br>C18H21N4O<br>309.3901<br>NCI-407323 | 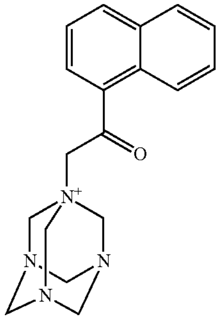 [SMILES: O=C(C[N+]12CN3CN(CN(C3)C1)C2)c1cccc2ccccc12] | −44.83921814 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| 1-(3-chloro-2-propenyl)-15,3,5,7-tetraazatricyclo[3.3.1.1~37~]decane (ACD/Name 4.0) C9H16ClN4 215.7052 NCI-172971 | 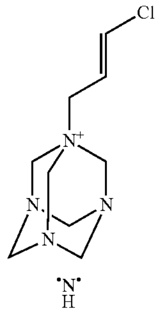 | −44.6733284 |
| 2-(1-piperazinyl)-N-(4-pyridinylmethyl)ethanamine (ACD/Name 4.0) C12H20N4 220.3168 NCI-66185 | 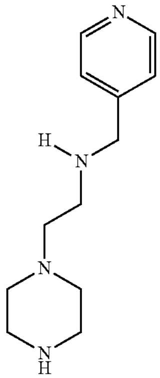 [SMILES: c1cc(CNCCN2CCNCC2)ccn1] | −44.53232956 |
| 1-(7-(1-piperidinyl)-3-((2-(1-piperidinyl)tetrahydro-3-furanyl)oxy)hexahydrofuro[3,4-b][1,4]dioxin-2-yl)piperidine (ACD/Name 4.0) C25H43N3O5 465.6318 NCI-76150 | 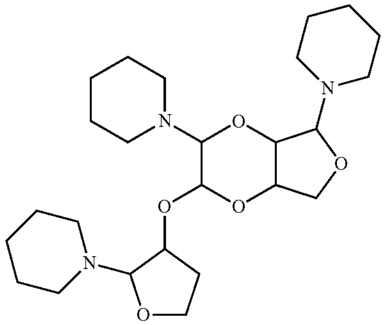 [SMILES: C1CCN(C2OCCC2OC2OC3COC(N4CCCCC4)C3OC2N2CCCCC2)CC1] | −44.42290878 |
| ethyl 3-((2-chloro-5-(hydroxy(oxido)amino)-6-methylhexahydro-4-pyrimidinyl)amino)propanoate (ACD/Name 4.0) C10H19ClN4O4 294.7375 NCI-134514 | 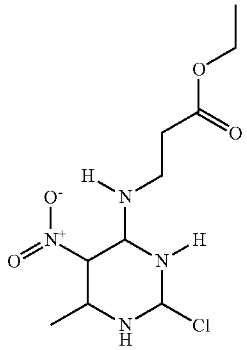 [SMILES: CCOC(=O)CCNC1NC(Cl)NC(C)C1[N+](=O)[O-]] | −44.3615036 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 1,2-dichloro-N1,N1,N1,N1,N2,N2,N2,N2-octamethyl-1,1,2,2-ethanetetramine (ACD/Name 4.0) C10H24Cl2N4 271.2324 NCI-137877 | 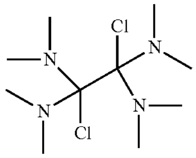 | −44.336586 |
| (1,3-dioxo-1,3-dihydro-2H-inden-2-ylidene)((2-hydroxyethyl)amino)acetonitrile (ACD/Name 4.0) C13H10N2O3 242.2336 NCI-379390 | 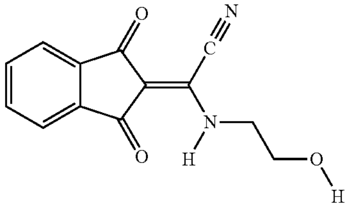 [SMILES: N#CC(NCCO)=C1C(=O)c2ccccc2C1=O] | −44.28065491 |
| tetradecahydro-2,3-phenazinediamine (ACD/Name 4.0) C12H24N4 224.3484 NCI-667746 | 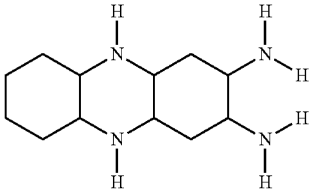 [SMILES: NC1CC2NC3CCCCC3NC2CC1N] | −44.26662445 |
| N1-(2-(4-amino(methyl)anilino)ethyl)-N1-(2-chloroethyl)-1,4-benzenediamine (ACD/Name 4.0) C17H23ClN4 318.8485 NCI-134445 | 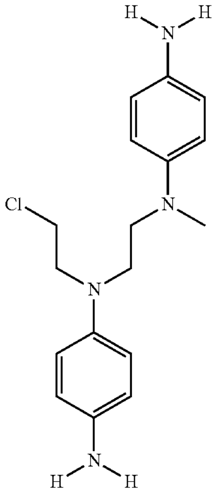 [SMILES: CN(CCN(CCCl)c1ccc(N)cc1)c1ccc(N)cc1] | −44.09951782 |
| 1-(2,3-dibromo-2-propenyl)-15,3,5,7-tetraazatricyclo[3.3.1.1~3,7~]decane (ACD/Name 4.0) C9H15Br2N4 339.0523 NCI-168615 | 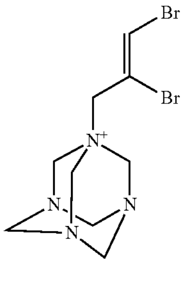 [SMILES: Br/C=C(\Br)C[N+]12CN3CN(CN(C3)C1)C2] | −44.03179932 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| N1,N4-bis(4-(4,5-dihydro-1H-imidazol-2-yl)phenyl)-2-(methylthio)terephthalamide (ACD/Name 4.0) C27H26N6O2S 498.6014 NCI-72382 | 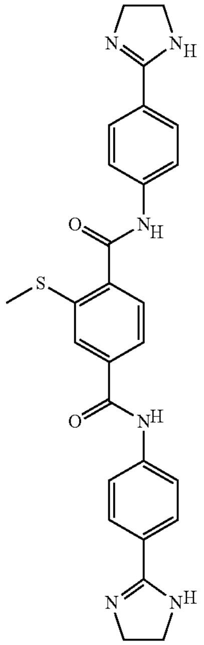 | −44.02162552 |
| 4-((4-((2,4-dihydroxy-3-quinolinyl)diazenyl)phenyl)diazenyl) benzenesulfonic acid (ACD/Name 4.0) C21H15N5O5S 449.44 NCI-45588 | 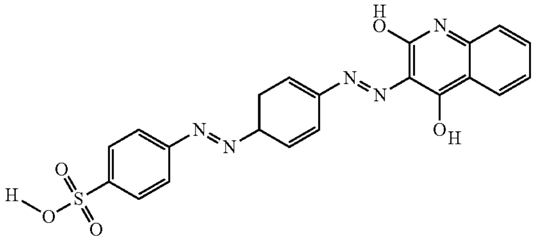 | −43.9335556 |
| 2,4,6-triphenyl-1,3,5-triazabicyclo[3.1.0]hexane (ACD/Name 4.0) C21H19N3 313.4012 NCI-634537 | 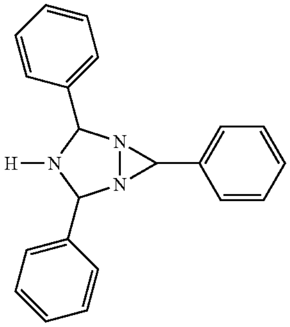 [SMILES: c1ccc(C2NC(c3ccccc3)N3C(c4ccccc4)N23)cc1] | −43.88329315 |
| 1-allyl-15,3,5,7-tetraazatricyclo[3.3.1.1~3,7~]decane (ACD/Name 4.0) C9H17N4 181.2601 NCI-5062 | 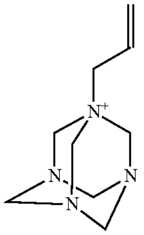 | −43.86736679 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| 1-(7-(1-piperidinyl)-3-((2-(1-piperidinyl)tetrahydro-3-furanyl)oxy)hexahydrofuro[3,4-b][1,4]dioxin-2-yl)piperidine (ACD/Name 4.0) C25H43N3O5 465.6318 NCI-76150 | 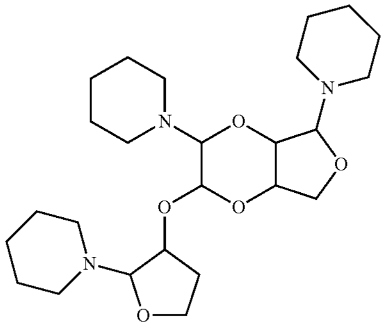 [SMILES: C1CCN(C2OCCC2OC2OC3COC(N4CCCCC4)C3OC2N2CCCCC2)CC1] | −43.79950333 |
| N1-(2-amino-2-methylpropyl)-2-methyl-1,2-propanediamine (ACD/Name 4.0) C8H21N3 159.274 NCI-17721 | 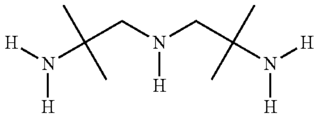 | −43.76238632 |
| 1-(4-chloro-2-butenyl)-15,3,5,7-tetraazatricyclo[3.3.1.1~3,7~]decane (ACD/Name 4.0) C10H18ClN4 229.732 NCI-30049 | 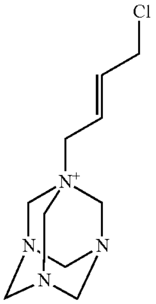 [SMILES: ClC/C=C/C[N+]12CN3CN(CN(C3)C1)C2] | −43.6402359 |
| Prospidin C18H36Cl2N4O2 411.414 NCI-166100 | 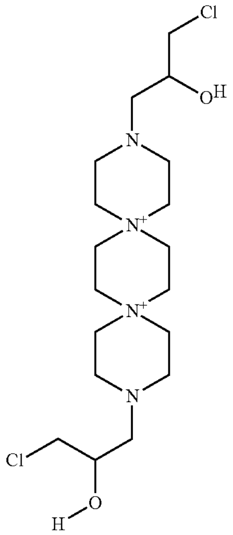 | −43.60018158 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| Bimolane<br>C20H32N6O6<br>452.5094<br>NCI-351358 | 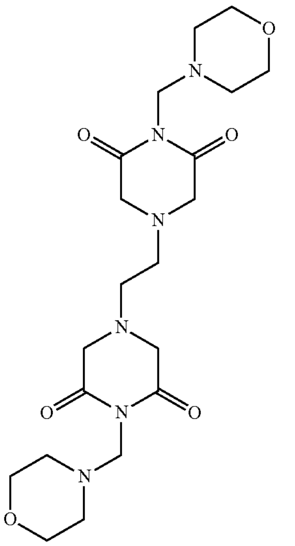 [SMILES: O=C1CN(CCN2CC(=O)N(CN3CCOCC3)C(=O)C2)CC(=O)N1CN1CCOCC1] | −43.56768036 |
| {4,8-Ethenobenzo[1,2-c:4,5-c']dipyrrole-1,3,5,7(2H,6H)-tetrone,} 3a, {4,4a,7a,8,8a-hexahydro-2,6-bis[(4-methyl-1-piperazinyl)methyl]-,} dihydrochloride<br>C24H34N6O4<br>470.5704<br>NCI-376597 | 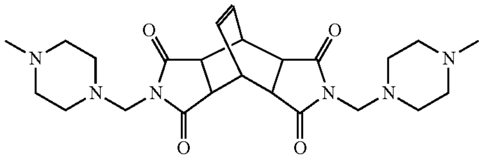 | −43.49063492 |
| 4-((1-(4-(hydroxy(oxido)amino)phenyl)-5-(4-morpholinyl)-4,5-dihydro-1H-1,2,3-triazol-4-yl)methyl)morpholine (ACD/Name 4.0)<br>C17H24N6O4<br>376.4144<br>NCI-363823 | 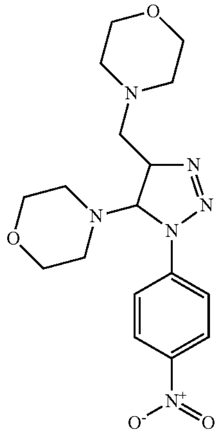 [SMILES: O=[N+]([O-])c1ccc(N2N=NC(CN3CCOCC3)C2N2CCOCC2)cc1] | −43.30677795 |
| 1,3-dimethyl-7-(2-(1-piperazinyl)ethyl)-3,7-dihydro-1H-purine-2,6-dione (ACD/Name 4.0)<br>C13H20N6O2<br>292.34<br>NCI-338290 | 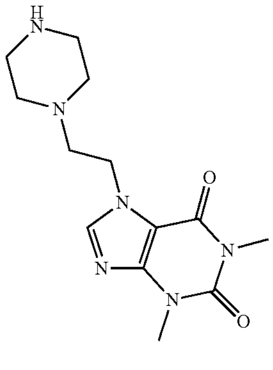 [SMILES: Cn1c(=O)c2c(ncn2CCN2CCNCC2)n(C)c1=O] | −43.30564117 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| (No Name)<br>C20H20Cl2N2O2<br>391.2962<br>NCI-15807 | 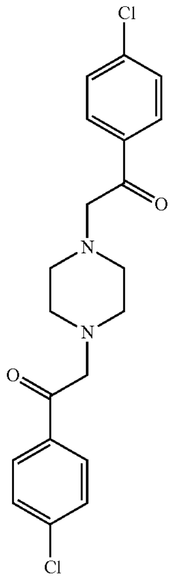 [SMILES: O=C(CN1CCN(CC(=O)c2ccc(Cl)cc2)CC1)c1ccc(Cl)cc1] | −43.22859955 |
| 1,4-bis(2,2,6,6-tetramethyl-1,2,3,6-tetrahydro-4-pyridinyl)piperazine (ACD/Name 4.0)<br>C22H40N4<br>360.5848<br>NCI-632539 | 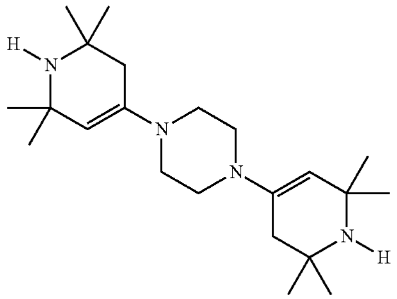 | −43.20852661 |
| N-hexyl-N-methyl-1,3,5-triazatricyclo[3.3.1.1~3.7~]decan-7-amine (ACD/Name 4.0)<br>C14H28N4<br>252.402<br>NCI-281707 | 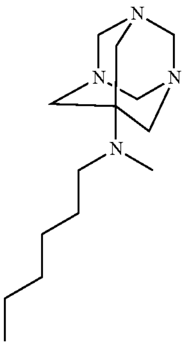 [SMILES: CCCCCCN(C)C12CN3CN(CN(C3)C1)C2] | −43.18684769 |
| 3-(1-azepanylmethyl)-1-methyl-5-phenyl-4-piperidinol (ACD/Name 4.0)<br>C19H30N2O<br>302.4588<br>NCI-400794 | 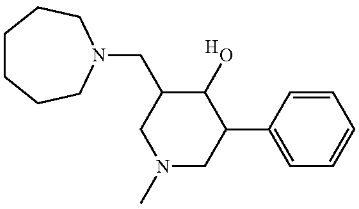 | −43.02958679 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| 2-(15,3,5,7-tetraazatricyclo[3.3.1.1~3,7~]dec-1-yl)ethanol (ACD/Name 4.0)<br>C8H17N4O<br>185.2485<br>NCI-206142 | 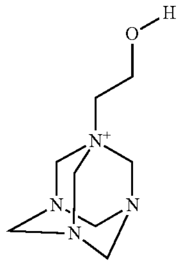 [SMILES: OCC[N+]12CN3CN(CN(C3)C1)C2] | −43.01359558 |
| N-ethyl-N-methyl-1,3,5-triazatricyclo[3.3.1.1~3,7~]decan-7-amine (ACD/Name 4.0)<br>C10H20N4<br>196.2948<br>NCI-281709 | 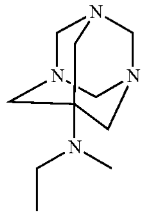 | −42.94138336 |
| tetradecahydro-2,3-phenazinediamine (ACD/Name 4.0)<br>C12H24N4<br>224.3484<br>NCI-667746 | 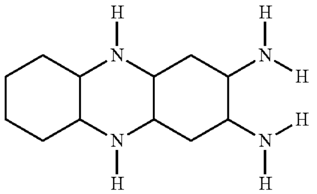 [SMILES: NC1CC2NC3CCCCC3NC2CC1N] | −42.85706711 |
| 1-(7-methyl-8-(3,4,5-trimethoxyphenyl)-7,8-dihydro-6H-[1,3]dioxolo[4,5-g]chromen-6-yl)hydrazine (ACD/Name 4.0)<br>C20H24N2O6<br>388.4194<br>NCI-667918 | 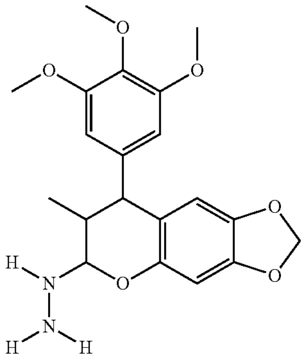 [SMILES: COc1cc(C2c3cc4c(cc3OC(NN)C2C)OCO4)cc(OC)c1OC] | −42.81098938 |
| 1-(2-oxiranylmethyl)-15,3,5,7-tetraazatricyclo[3.3.1.1~3,7~]decane (ACD/Name 4.0)<br>C9H17N4O<br>197.2595<br>NCI-177979 | 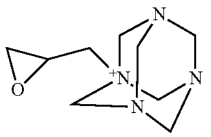 [SMILES: C1OC1C[N+]12CN3CN(CN(C3)C1)C2] | −42.72693634 |
| 1-benzyl-15,3,5,7-tetraazatricyclo[3.3.1.1~3,7~]decane (ACD/Name 4.0)<br>C13H19N4<br>231.3199<br>NCI-10408 | 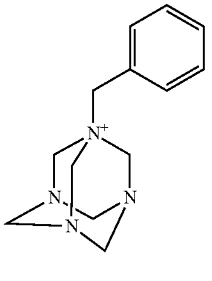 [SMILES: c1ccc(C[N+]23CN4CN(CN(C4)C2)C3)cc1] | −42.64362335 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| N-(2-((2-pyrrolidinylcarbonyl)amino)ethyl)-2-pyrrolidinecarboxamide (ACD/Name 4.0) C12H22N4O2 254.3314 NCI-621603 | 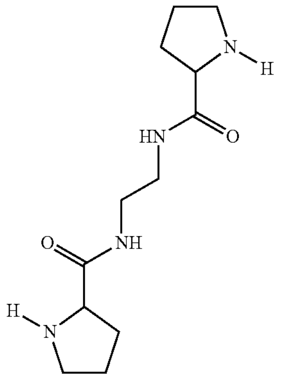 [SMILES: O=C(NCCNC(=O)C1CCCN1)C1CCCN1] | −42.60683441 |
| 1-(15,3,5,7-tetraazatricyclo[3.3.1.1~3,7~]dec-1-yl)acetone (ACD/Name 4.0) C9H17N4O 197.2595 NCI-177977 | 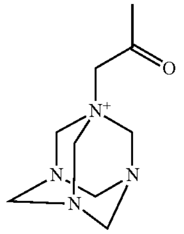 | −42.55291367 |
| 2,4,6-tris(4-chlorophenyl)-1,3,5-triazinane (ACD/Name 4.0) C21H18Cl3N3 418.7523 NCI-135155 | 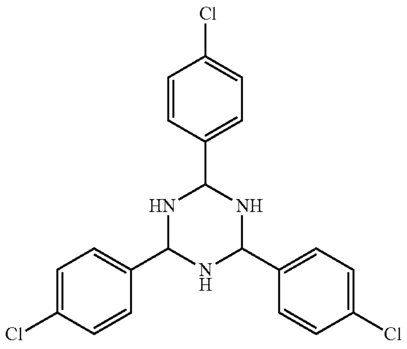 [SMILES: Clc1ccc(C2NC(c3ccc(Cl)cc3)NC(c3ccc(Cl)cc3)N2)cc1] | −42.54439163 |
| N1,N2-bis(1-piperazinylmethyl)ethanedithioamide (ACD/Name 4.0) C12H24N6S2 316.4818 NCI-203396 | 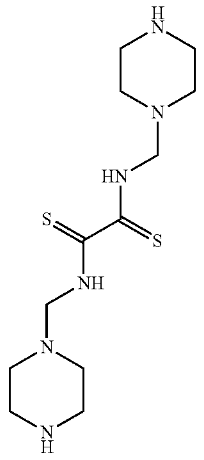 [SMILES: S=C(NCN1CCNCC1)C(=S)NCN1CCNCC1] | −42.53646088 |

TABLE 4-continued

| A list of identified topoisomerase II nuclear export signal inhibitors. | | |
|---|---|---|
| Compound Name/ Chemical Formula/ Molecular Weight/ NCI Number | Structure | Docking Score |
| 5-((bis(methylamino)methyl)imino)-1,3,3,4-tetramethyl-1,4,2-diazaphospholidin-2-ol 2-oxide (ACD/Name 4.0) C9H22N5O2P 263.2789 NCI-676758 | 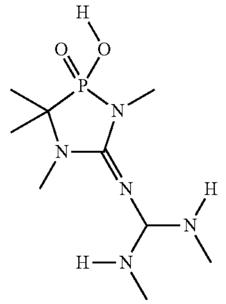 | −42.50998688 |
| 1-(2-chloro-2-propenyl)-15,3,5,7-tetraazatricyclo[3.3.1.1~3,7~]decane (ACD/Name 4.0) C9H16ClN4 215.7052 NCI-172855 | 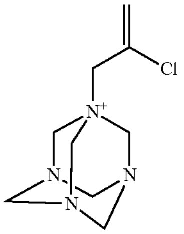 | −42.36437988 |
| 1-(2-oxiranylmethyl)-15,3,5,7-tetraazatricyclo[3.3.1.1~3,7~]decane (ACD/Name 4.0) C9H17N4O 197.2595 NCI-177979 | 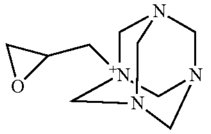 [SMILES: C1OC1C[N+]12CN3CN(CN(C3)C1)C2] | −42.34187317 |
| 1-bromo-15,3,5,7-tetraazatricyclo[3.3.1.1~3,7~]decane (ACD/Name 4.0) C6H12BrN4 220.0916 NCI-203305 | 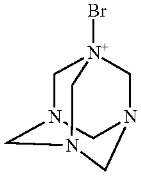 [SMILES: Br[N+]12CN3CN(CN(C3)C1)C2] | −42.31611252 |
| 2,4,6-triisopropyl-1,3,5-triazabicyclo[3.1.0]hexane (ACD/Name 4.0) C12H25N3 211.3496 NCI-254951 | 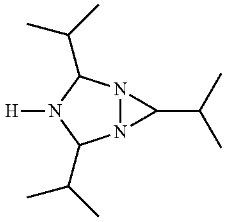 | −42.31566238 |
| 1,4-bis(1H-imidazol-2-ylmethyl)piperazine (ACD/Name 4.0) C12H18N6 246.3144 NCI-116533 | 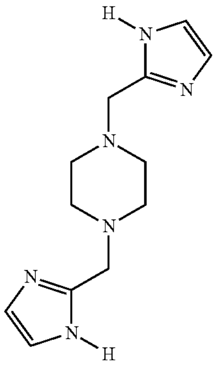 [SMILES: c1c[nH]c(CN2CCN(Cc3ncc[nH]3)CC2)n1] | −42.28594971 |

TABLE 4-continued

A list of identified topoisomerase II nuclear export signal inhibitors.

| Compound Name/ Chemical Formula/ Molecular Weight/ NCI Number | Structure | Docking Score |
|---|---|---|
| N-(2-(1-pyrrolidinyl)ethyl)-3,4-dihydro-2(1H)-isoquinolinamine (ACD/Name 4.0) C15H23N3 245.3668 NCI-23428 | 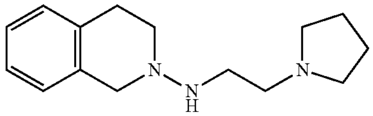 [SMILES: c1ccc2c(c1)CCN(NCCN1CCCC1)C2] | −42.14746094 |
| N1,N4-bis(4-(4,5-dihydro-1H-imidazol-2-yl)phenyl)terephthalamide (ACD/Name 4.0) C26H24N6O2 452.5146 NCI-35843 | 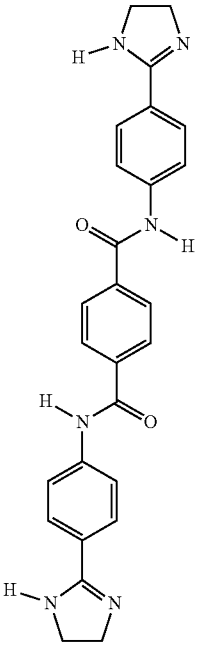 [SMILES: O=C(Nc1ccc(C2=NCCN2)cc1)c1ccc(C(=O)Nc2ccc(C3=NCCN3)cc2)cc1] | −42.14398193 |
| N-isobutyl-1,3,5-triazatricyclo[3.3.1.1~3.7~]decan-7-amine (ACD/Name 4.0) C11H22N4 210.3216 NCI-281703 | 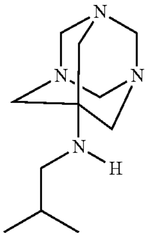 | −42.12605286 |

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a topoisomerase II nuclear export inhibitor, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating an oncogenic disease or reducing oncogenic potential of a cell, comprising administering a therapeutically effective amount of a topoisomerase II nuclear export signal inhibitor to a patient or contacting the cell with the therapeutically effective amount of a topoisomerase II nuclear export signal inhibitor;

wherein the topoisomerase II nuclear export signal inhibitor is NCI-9138, NCI-155877, NCI-35847, or an having the backbone structure

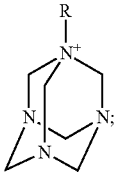

wherein the oncogenic disease is multiple myeloma, or breast cancer; and co-administering the topoisomerase II nuclear export signal inhibitor with an intercalating topoisomerase II inhibitor, wherein the topoisomerase II inhibitor is administered at between 1.6 to 24 hours after administration of the topoisomerase II nuclear export signal inhibitor, or at about 4 hours after administration of the topoisomerase II nuclear export signal inhibitor.

2. The method of claim 1, wherein the topoisomerase II nuclear export signal inhibitor is NCI-35847, NCI-80640, NCI-9138, or NCI-155877.

3. The method of claim 2, wherein the topoisomerase II nuclear export signal inhibitor is NCI-80640, NCI-9138, or NCI-15587.

4. The method of claim 1, wherein the topoisomerase II nuclear export signal inhibitor is administered to reach a local concentration between 2 μM and 100 μM.

5. The method of claim 1, wherein the topoisomerase II inhibitor is amsacrine, etoposide, etoposide phosphate, teniposide, doxorubicin, epirubicin, daunomycin, mitoxantrone, idarubicin, or VP16.

6. The method of claim 1, wherein the topoisomerase II inhibitor is doxorubicin.

7. The method of claim 1, wherein the topoisomerase II inhibitor is doxorubicin administered at 2 μM.

8. A method of treating an oncogenic disease, comprising administering a therapeutically effective amount of a topoisomerase II inhibitor and a therapeutically effective amount of a topoisomerase II nuclear export signal inhibitor to a patient;

wherein the oncogenic disease is multiple myeloma;

wherein the topoisomerase II nuclear export signal inhibitor is NCI-35847, NCI-80640, NCI-9138, or NCI-155877; and wherein the topoisomerase II inhibitor is administered at between 1.6 to 24 hours after administration of the topoisomerase II nuclear export signal inhibitor, or at about 4 hours after administration of the topoisomerase II nuclear export signal inhibitor.

9. The method of claim 8, wherein the topoisomerase II nuclear export signal inhibitor is administered to reach a local concentration of between 2 μM and 25 μM.

10. The method of claim 8, wherein the topoisomerase II inhibitor is administered at between 1.6 to 24 hours after administration of the topoisomerase II nuclear export signal inhibitor, or at about 4 hours after administration of the topoisomerase II nuclear export signal inhibitor.

11. The method of claim 8, wherein the topoisomerase II inhibitor is amsacrine, etoposide, etoposide phosphate, teniposide, doxorubicin, epirubicin, daunomycin, mitoxantrone, and idarubicin.

12. The method of claim 11, wherein the topoisomerase II inhibitor is doxorubicin.

13. The method of claim 11, wherein the topoisomerase II inhibitor is doxorubicin administered at 2 μM.

14. The method of claim 1, wherein the topoisomerase inhibitor is administered at about 1.6 after administration of the topoisomerase II nuclear export signal inhibitor, about 20 hours after administration of the topoisomerase II nuclear export signal inhibitor, or about 24 hours after administration of the topoisomerase II nuclear export signal inhibitor.

15. The method of claim 1, wherein the topoisomerase inhibitor is administered at 20 hours after administration of the topoisomerase II nuclear export signal inhibitor, or 24 hours after administration of the topoisomerase II nuclear export signal inhibitor.

16. The method of claim 4, wherein the topoisomerase II nuclear export signal inhibitor is administered to reach a local concentration between 2 μM and 25 μM.

* * * * *